United States Patent
Rützler et al.

(10) Patent No.: US 10,011,597 B2
(45) Date of Patent: Jul. 3, 2018

(54) DERIVATIVES OF 2-(1,2,4-TRIAZOL-3-YLSULFANYL)-N-1,3,4-THIADIAZOL-2-YL ACETAMIDE WHICH ARE USEFUL FOR THE TREATMENT OF INTER ALIA DIABETES

(71) Applicant: APOGLYX AB, Lund (SE)

(72) Inventors: Michael Rützler, Lund (SE); Thomas Brimert, Blentarp (SE); Klaus Dreisch, Lund (SE); Johan Evenäs, Lund (SE); Joakim Larsson, Lomma (SE)

(73) Assignee: APOGLYX AB, Lund (SE)

( * ) Notice: Subject to any disclaimer, the term of this patent is extended or adjusted under 35 U.S.C. 154(b) by 0 days.

(21) Appl. No.: 15/522,958

(22) PCT Filed: Oct. 28, 2015

(86) PCT No.: PCT/EP2015/075007
§ 371 (c)(1),
(2) Date: Apr. 28, 2017

(87) PCT Pub. No.: WO2016/066696
PCT Pub. Date: May 6, 2016

(65) Prior Publication Data
US 2017/0320869 A1    Nov. 9, 2017

(30) Foreign Application Priority Data

Oct. 29, 2014   (SE) ........................................ 1451289

(51) Int. Cl.
| | |
|---|---|
| *A61K 31/4196* | (2006.01) |
| *A61K 31/433* | (2006.01) |
| *C07D 417/12* | (2006.01) |
| *C07D 417/14* | (2006.01) |
| *C07D 403/12* | (2006.01) |
| *C07D 249/12* | (2006.01) |
| *C07D 285/135* | (2006.01) |

(52) U.S. Cl.
CPC ........ *C07D 417/12* (2013.01); *A61K 31/4196* (2013.01); *A61K 31/433* (2013.01); *C07D 249/12* (2013.01); *C07D 285/135* (2013.01); *C07D 403/12* (2013.01); *C07D 417/14* (2013.01)

(58) Field of Classification Search
None
See application file for complete search history.

(56) References Cited

PUBLICATIONS

Jelen et al., Journal of Biological Chemistry, vol. 286, No. 52, pp. 44319-44325 (2011).*

\* cited by examiner

*Primary Examiner* — Alicia L Otton
(74) *Attorney, Agent, or Firm* — Polsinelli PC; Ron Galant

(57) ABSTRACT

Disclosed are compounds, pharmaceutical compositions and methods for modulating aquaporin 9.

19 Claims, No Drawings

DERIVATIVES OF 2-(1,2,4-TRIAZOL-3-YLSULFANYL)-N-1,3,4-THIADIAZOL-2-YL ACETAMIDE WHICH ARE USEFUL FOR THE TREATMENT OF INTER ALIA DIABETES

FIELD OF THE INVENTION

The present invention relates to compounds for modulating aquaporins and in particular, Aquaporin 9 (AQP9). The invention also relates to pharmaceutical compositions comprising the compounds and a method of modulating AQP9, e.g. for treating diabetes, in a subject comprising administration of the compounds.

BACKGROUND

Aquaporins are widely but differentially expressed in plant and animal tissues. These transmembrane channels facilitate passive transport of water and specific solutes, like urea and glycerol, thereby crucially affecting fluid balance in mammalian and other organisms. Members of these channels have been shown to contribute to the pathology of various diseases and disorders, including metabolic disease, inflammatory disease, bone disease, atherosclerosis, allergic diseases, as well as autoimmune pathologies such as rheumatoid arthritis. Mammalian aquaporins can be divided into at least three subfamilies: the aquaporin subfamily that conducts water, the aquaglyceroporins, which allow the passage of water and small uncharged molecules like glycerol and urea, and a third group of unorthodox aquaporins which remain poorly characterized at present.

Aquaporin 3, 7 and 9 belong to the aquaglyceroporins and are structurally related, but expressed in different cells and tissues and thus have been ascribed specific functions. Aquaporin 9 (AQP9) is a glycerol channel that is expressed in liver, lung, and skin tissues, gastrointestinal tissues, tissues of the male and female reproductive tract, and hematopoietic cells (The Human Protein Atlas, www.proteinatlas.org). Thus, AQP9 channels might represent good targets for drug development since agents modulating these channels would be useful in the treatment of disorders and diseases, where its function or dysfunction contributes to the development or maintenance of disease. Indeed, AQP9 has been implicated in pathophysiological processes in a variety of diseases, such as diabetes, atherosclerosis, disuse osteoporosis, non-alcoholic fatty liver disease, acute kidney injury, kidney ischemia-reperfusion injury, inflammatory diseases including but not limited to inflammatory bowel disease, psoriasis, allergic contact dermatitis, and rheumatoid arthritis.

Approximately 90% of all plasma glycerol is converted to glucose by the liver. In states of dysregulated glucose metabolism, such as type 2 diabetes (characterized by elevated blood glucose levels and insulin resistance), gluconeogenesis from glycerol accounts for 10% of hepatic glucose production in patients (Puhakainen, I. et. al., *J. Clin. Endocrinol. Metab.*, 1992, 75, 789-794). This amounts to a daily production of 500 mmol (about 90 gram) of glucose in average obese type 2 patients, compared to 150 mmol in healthy individuals of normal weight.

Studies of AQP9 knockout mice have clearly demonstrated the pathophysiological relevance of glycerol channels in liver through effects on glycerol metabolism. Specifically, AQP9 is essential for efficient glycerol uptake into hepatocytes and is crucial for hepatic glucose production. (Jelen et al, *J. Biol. Chem.*, 2011, 286, 44319-44325). In AQP9-deficient diabetic mice, blood glucose levels were normal 2 hours after a meal, while blood glucose was ~30% elevated in equally treated aquaporin 9 wildtype diabetic mice (Rojek, A. M., et al., *Proc. Natl. Acad. Sci. USA*, 2007, 104, 3609-3614). These results suggest that inhibition of AQP9 could reduce plasma glucose levels after a meal and that AQP9 is a potential drug target in diabetic treatment.

It would be desirable to provide compounds having high affinity for aquaporin 9 and the ability to modulate aquaporin 9 or to diminish deregulated hepatocyte glucose output in metabolic disease as characterized by hyperglycemia.

SUMMARY

Consequently, the present invention seeks to mitigate, alleviate, eliminate or circumvent one or more of the above-identified deficiencies in the art and disadvantages singly or in any combination by providing, in one aspect, a compound of Formula (I)

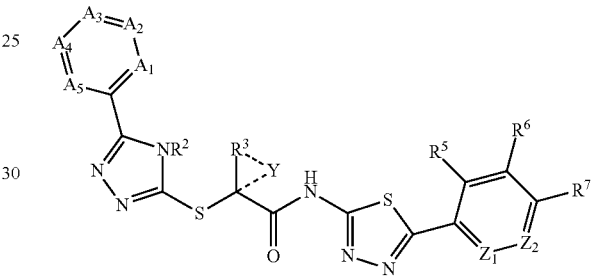

Formula (I)

or pharmaceutically acceptable salts and stereoisomers thereof, wherein:

$A_1$, $A_2$, $A_3$, $A_4$, and $A_5$ are independently selected from the group consisting of CH, $CR^2$ and N;

Y is absent or is selected from $CH_2$ or $CHC_1$-$C_5$ alkyl;

- - - - . is a single bond when Y is $CH_2$ or $CHC_1$-$C_5$ alkyl;

$Z_1$ and $Z_2$ are independently selected from the group consisting of CH and N;

$R^1$ is independently selected from the group consisting of halogen, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^2$ is selected from the group consisting of $C_1$-$C_6$ alkyl, $C_1$-$C_6$ alkylene-$OR^{4a}$, $C_1$-$C_6$ alkylene-$N(R^{4a})(R^{4b})$, $C_1$-$C_6$ alkylene-$C(O)N(R^{4a})(R^{4b})$, $C_1$-$C_6$ alkylene-$C(O)OR^{4a}$, $C_1$-$C_3$ alkylene-$C_3$-$C_6$ cycloalkyl, and $C_3$-$C_5$ cycloalkyl;

$R^3$ is selected from the group consisting of H, $C_1$-$C_6$ alkyl, and $C_1$-$C_6$ alkylene-$C(O)N(R^{4a})(R^{4b})$ when Y is absent or, $R^3$ is selected from $C_1$-$C_6$ alkyl, and $C_1$-$C_6$ alkylene-$C(O)N(R^{4a})(R^{4b})$ when Y is $CH_2$ or $CHC_1$-$C_5$ alkyl;

$R^{4a}$ and $R^{4b}$ are independently selected from H, $C_1$-$C_4$ alkyl, and cyclopropyl;

$R^5$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^6$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^7$ is selected from the group consisting of H, halogen, CN, OH, $C_1$-$C_6$ alkyl, $C_3$-$C_6$ cycloalkyl, $C_1$-$C_6$ alkyloxy, $O(CH_2)_mO(CH_2)_nCH_3$, $O(CH_2)_mN(R^{4a})(R^{4b})$, $OSO_2CH_3$, $SO_2C_1$-$C_6$ alkyl, $C_1$-$C_6$ alkylene-$SO_2C_1$-$C_6$ alkyl, $SO_2C_3$-$C_6$ cycloalkyl, $C_1$-$C_6$ alkylene-$SO_2C_3$-$C_6$ cycloalkyl, $SC_1$-$C_6$ alkyl, $SC_3$-$C_6$ cycloalkyl, $C_1$-$C_6$ alkylene-$SC_1$-$C_6$ alkyl, $C_1$-$C_6$ alkylene-$SC_3$-$C_6$ cycloalkyl, and $S(O)(NR^{8a})(R^{8b})$;

$R^{8a}$ is selected from H, $C_1$-$C_6$ alkyl, and $C_3$-$C_6$ cycloalkyl;
$R^{8b}$ is $C_1$-$C_6$ alkyl or $C_3$-$C_6$ cycloalkyl;
m is an integer selected from the group consisting of 1, 2, and 3;
n is an integer selected from the group consisting of 0, 1, and 2;
with the proviso that $R^5$, $R^6$, and $R^7$ cannot be H simultaneously; and
with the proviso the compound is not:

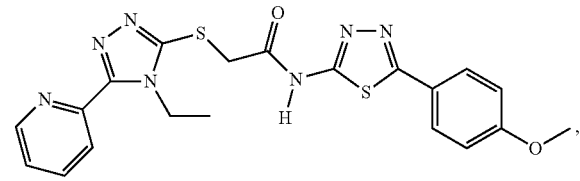

,

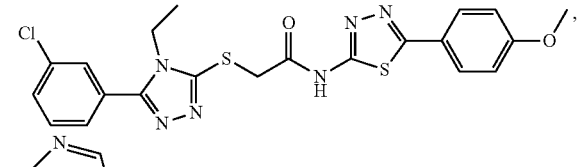

,

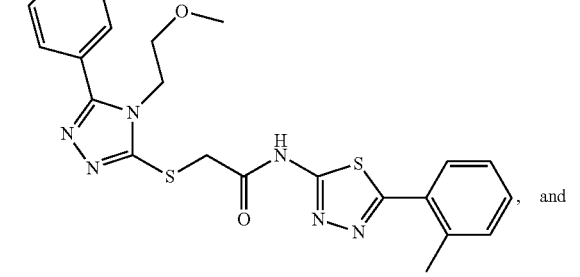

, and

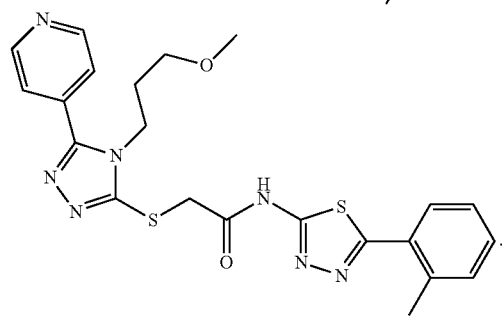

.

According to another aspect, there is provided a pharmaceutical composition comprising a compound of the herein above described type and a pharmaceutically acceptable diluent, excipient or carrier.

According to another aspect, there is provided a compound or pharmaceutical composition of the herein above described type, or a compound selected from the group consisting of:

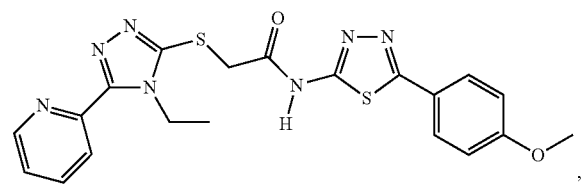

,

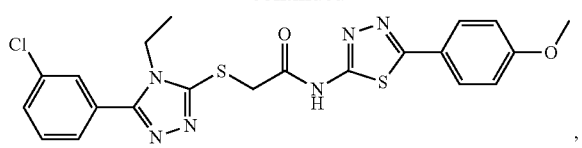

,

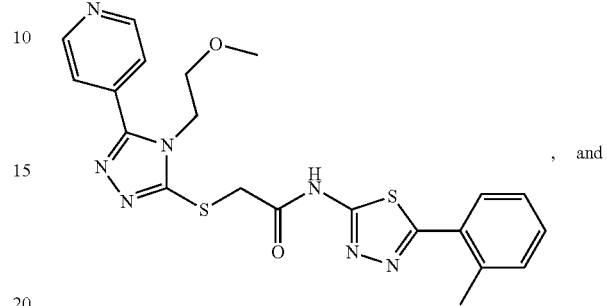

, and

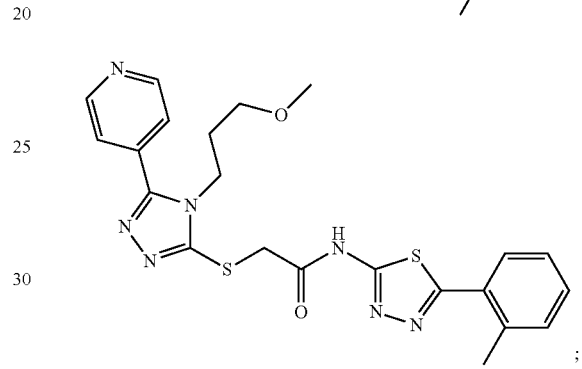

;

for use in treating diabetes.

According to another aspect, there is provided a compound or pharmaceutical composition of the herein above described type, or a compound selected from the group consisting of:

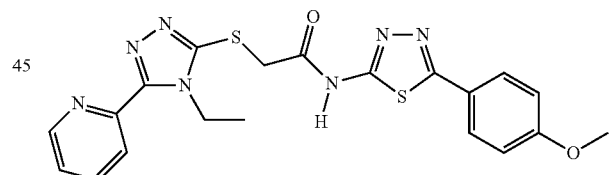

,

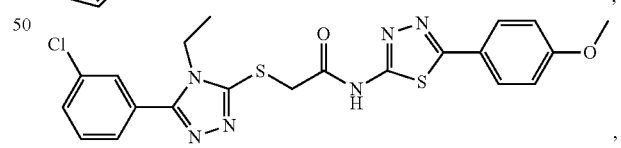

,

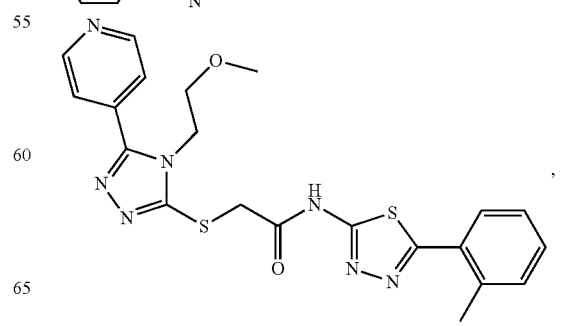

, and

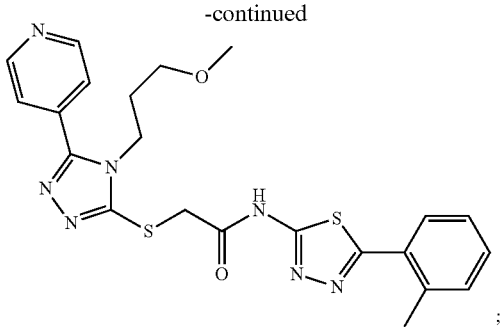

for use in treatment of disorders and diseases, where the function or dysfunction of AQP9 contributes to the development or maintenance of disease, such as diabetes, atherosclerosis, disuse osteoporosis, non-alcoholic fatty liver disease, acute kidney injury, kidney ischemia-reperfusion injury, inflammatory diseases, e.g. inflammatory bowel disease, psoriasis, allergic contact dermatitis or rheumatoid arthritis.

According to yet another aspect, there is provided a non-therapeutic use of a compound or pharmaceutical composition of the herein above described type, or a compound selected from the group consisting of:

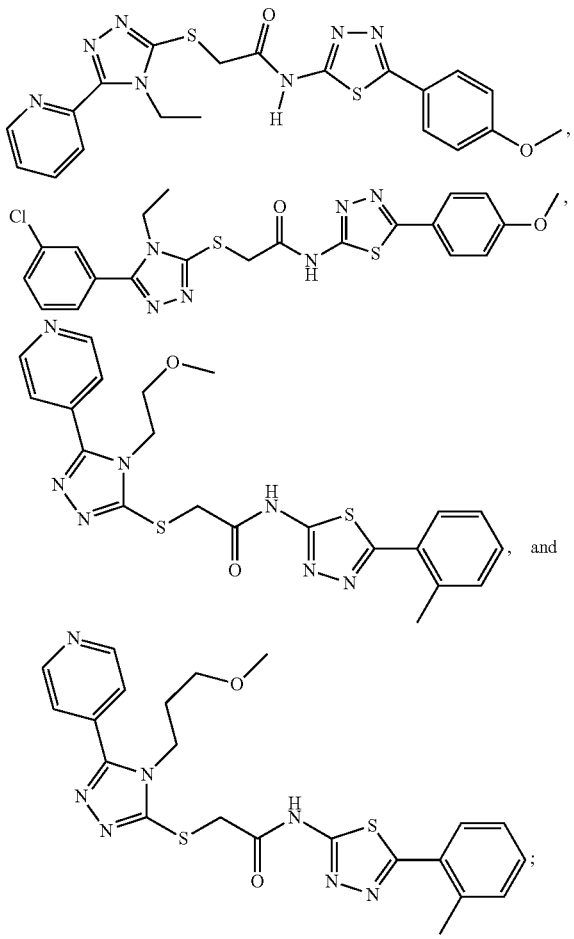

for modulating the activity of an aquaporin 9 protein.

Further, advantageous features of various embodiments of the invention are defined in the dependent claims and within the detailed description below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$-$C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—$CH_3CH(CH_3)CH_2$—, $(CH_3)_3C$—, $CH_3(CH_2)_3CH_2$— and $CH_3(CH_2)_4CH_2$—.

As used herein, "alkyl" refers to a straight or branched hydrocarbon chain group that is fully saturated (no double or triple bonds). The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "cycloalkyl" refers to a completely saturated (no double bonds) monocyclic hydrocarbon ring system. Cycloalkyl groups may range from $C_3$ to $C_{10}$, such as from $C_3$ to $C_6$. Typical cycloalkyl groups include, but are in no way limited to, cyclopropyl, cyclobutyl, cyclopentyl, cyclohexyl, and the like.

An "alkylene" is a straight-chained tethering group, forming bonds to connect molecular fragments via their terminal carbon atoms. The alkylene may be a medium size alkylene having 1 to 6 carbon atoms, such as "$C_1$-$C_6$." The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom.

As used herein, "alkyloxy" refers to the group —OR wherein R is an alkyl. Non-limiting examples of alkyloxy groups include methoxy, ethoxy, n-propoxy, 1-methylethoxy (isopropoxy), n-butoxy, iso-butoxy, sec-butoxy, and tert-butoxy. However, the alkyl in the alkyloxy group does not include cycloalkyl groups.

As used herein, "halogen" refers to F (fluoro), Cl (chloro), Br (bromo) or I (iodo).

A dashed bond, - - - - -, represents an optional single bond between the atoms forming the bond. The dashed bond may be absent or present. In the present invention, dashed bonds are depicted in formula (I) between Y and $R^3$ and between Y and C as described above. In formula (I) when Y is absent there is no bond between Y and $R^3$ and no bond between Y and the C atom that has the adjacent S atom and C=O group. In formula (I) when Y is $CH_2$ there is a single bond between Y and $R^3$ and a single bond between Y and the C atom that has the adjacent S atom and C=O group A "cyano" group refers to a "—CN" group.

A "hydroxy" group or "hydroxyl" group refers to an "—OH" group.

The term "stereoisomers" refers to compounds that have the same molecular formula and sequence of bonded atoms but differ in the three-dimensional orientations of their atoms in space. Non-limiting examples of stereoisomers include enantiomers, diastereomers, conformers and atropisomers.

It is understood that, in any compound disclosed herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. Further, compounds provided herein may be scalemic mixtures. Likewise, all tautomeric forms are also intended to be included. As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is also understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates. Pharmaceutically acceptable solvates and hydrates are complexes of a compound with one or more solvent of water molecules, or 1 to about 100, or 1 to about 10, or one to about 2, 3 or 4, solvent or water molecules.

The term "physiologically acceptable" defines a carrier or diluent that does not abrogate the biological activity and properties of the compound. As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "a therapeutically effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

Compounds

As described above, in one aspect of the invention a compound of Formula (I)

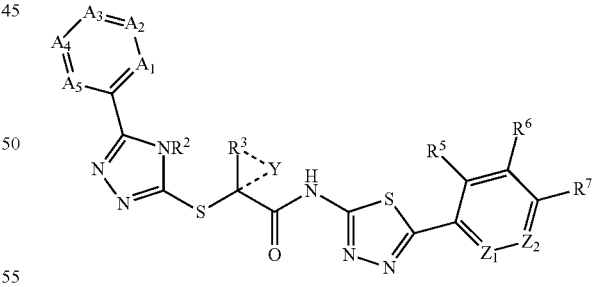

Formula (I)

or pharmaceutically acceptable salts and stereoisomers thereof, wherein:

$A_1$, $A_2$, $A_3$, $A_4$, and $A_5$ are independently selected from the group consisting of CH, $CR^1$ and N;

Y is absent or is selected from $CH_2$ or $CHC_1$-$C_5$ alkyl;

- - - - . is a single bond when Y is $CH_2$ or $CHC_1$-$C_5$ alkyl;

$Z_1$ and $Z_2$ are independently selected from the group consisting of CH and N;

$R^1$ is independently selected from the group consisting of halogen, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^2$ is selected from the group consisting of $C_1$-$C_6$ alkyl, $C_1$-$C_6$ alkylene-$OR^{4a}$, $C_1$-$C_6$ alkylene-$N(R^{4a})(R^{4b})$, $C_1$-$C_6$ alkylene-$C(O)N(R^{4a})(R^{4b})$, $C_1$-$C_6$ alkylene-$C(O)OR^{4a}$, $C_1$-$C_3$ alkylene-$C_3$-$C_6$ cycloalkyl, and $C_3$-$C_5$ cycloalkyl;

$R^3$ is selected from the group consisting of H, $C_1$-$C_6$ alkyl, and $C_1$-$C_6$ alkylene-$C(O)N(R^{4a})(R^{4b})$ when Y is absent or, $R^3$ is selected from $C_1$-$C_6$ alkyl, and $C_1$-$C_6$ alkylene-$C(O)N(R^{4a})(R^{4b})$ when Y is $CH_2$ or $CHC_1$-$C_5$ alkyl;

$R^{4a}$ and $R^{4b}$ are independently selected from H, $C_1$-$C_4$ alkyl, and cyclopropyl;

$R^5$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^6$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^7$ is selected from the group consisting of H, halogen, CN, OH, $C_1$-$C_6$ alkyl, $C_3$-$C_6$ cycloalkyl, $C_1$-$C_6$ alkyloxy, $O(CH_2)_mO(CH_2)_nCH_3$, $O(CH_2)_mN(R^{4a})(R^{4b})$, and $OSO_2CH_3$, $SO_2C_1$-$C_6$ alkyl, $C_1$-$C_6$ alkylene-$SO_2C_1$-$C_6$ alkyl, $SO_2C_3$-$C_6$ cycloalkyl, $C_1$-$C_6$ alkylene-$SO_2C_3$-$C_6$ cycloalkyl, $SC_1$-$C_6$ alkyl, $SC_3$-$C_6$ cycloalkyl, $C_1$-$C_6$ alkylene-$SC_1$-$C_6$ alkyl, $C_1$-$C_6$ alkylene-$SC_3$-$C_6$ cycloalkyl, and $S(O)(NR^{8a})(R^{8b})$;

$R^{8a}$ is selected from H, $C_1$-$C_6$ alkyl, and $C_3$-$C_6$ cycloalkyl;

$R^{8b}$ is $C_1$-$C_6$ alkyl or $C_3$-$C_6$ cycloalkyl;

m is an integer selected from the group consisting of 1, 2, and 3;

n is an integer selected from the group consisting of 0, 1, and 2;

with the proviso that $R^5$, $R^6$, and $R^7$ cannot be H simultaneously; and with the proviso the compound is not:

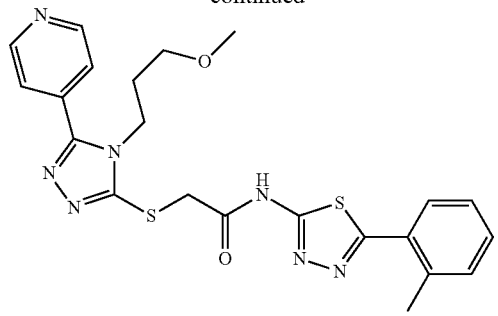

is provided.

In some embodiments of the compound described above, $R^1$ is independently selected from the group consisting of F, Cl, $CH_3$, and $OCH_3$.

According to an embodiment of the compound described above, $R^2$ is selected from the group consisting of $CH_3$, $CH_2CH_3$, and cyclopropyl. Without wishing to be bound by theory, it is believed that compounds wherein $R^2$ is hydrogen are significantly less active than compounds of the present invention wherein $R^2$ is selected from a defined list of variables above with respect to formula (I) which does not include hydrogen.

In other embodiments of the compound described above, $R^2$ is selected from the group consisting of $CH_2CH_2OH$, $CH_2CH_2CH_2OH$, $CH_2CH_2NH_2$, $CH_2C(O)NH_2$, and $CH_2CH_2C(O)OCH_3$.

In an embodiment of the compound described above, $R^3$ is H. Of course, when $R^3$ is H then Y is absent and there is no single bond between Y and $R^3$ and no single bond between Y and the C atom that has the adjacent S atom and C=O group.

In some embodiments of the compound described above, $R^{4a}$ and $R^{4b}$ are independently selected from H and $CH_3$.

According to another embodiment of the compound described above, $R^5$ is selected from the group consisting of H, F, and $OCH_3$. In one preferred embodiment of the compound described above, $R^5$ is H.

According to some embodiments of the compound described above, $R^6$ is selected from the group consisting of H, F, and $OCH_3$. In a preferred embodiment of the compound described above, $R^6$ is H.

In some embodiments of the compound described above, $R^7$ is selected from the group consisting of H, halogen, CN, OH, $C_1$-$C_6$ alkyl, $C_3$-$C_6$ cycloalkyl, $C_1$-$C_6$ alkyloxy, $O(CH_2)_mO(CH_2)_nCH_3$, $O(CH_2)_mN(R^{4a})(R^{4b})$, and $OSO_2CH_3$.

In some embodiments of the compound described above, $R^7$ is selected from the group consisting of $SO_2C_1$-$C_6$ alkyl, $C_1$-$C_6$ alkylene-$SO_2C_1$-$C_6$ alkyl, $SO_2C_3$-$C_6$ cycloalkyl, $C_1$-$C_6$ alkylene-$SO_2C_3$-$C_6$ cycloalkyl, $SC_1$-$C_6$ alkyl, $SC_3$-$C_6$ cycloalkyl, $C_1$-$C_6$ alkylene-$SC_1$-$C_6$ alkyl, and $C_1$-$C_6$ alkylene-$SC_3$-$C_6$ cycloalkyl. In other embodiments, $R^7$ is $S(O)(NR^{8a})(R^{8b})$.

In some embodiments of the compound described above, $R^7$ is selected from the group consisting of $SO_2CH_3$, $CH_2SO_2CH_3$, $SCH_3$, $S(O)(NH)CH_3$, $S(O)(NCH_3)CH_3$, $S(O)(NH)$cyclopropyl, and $S(O)(NCH_3)$cyclopropyl. In one embodiment of the compound described above, $R^7$ is selected from the group consisting of $SO_2CH_3$, $CH_2SO_2CH_3$, and $SCH_3$. In another embodiment, $R^7$ is selected from the group consisting of $S(O)(NH)CH_3$, $S(O)(NCH_3)CH_3$, $S(O)(NH)$cyclopropyl, and $S(O)(NCH_3)$cyclopropyl.

In another embodiment of the compound described above, $R^7$ is selected from the group consisting of H, F, OH, $OCH_3$, $OCH_2CH_2OCH_3$, and $OSO_2CH_3$. In a preferred embodiment of the compound described above, $R^7$ is F or $OCH_3$.

In some embodiments of the compound described above, Y is absent. Of course, when Y is absent then $R^3$ is selected from the group consisting of H, $C_1$-$C_6$ alkyl, and $C_1$-$C_6$ alkylene-$C(O)N(R^{4a})(R^{4b})$. Preferably however, when Y is absent, $R^3$ is H.

According to another embodiment of the compound described above, at least one of $A_1$, $A_2$, $A_3$, $A_4$, and $A_5$ is N. In a preferred embodiment of the compound described above, one of $A_1$, $A_2$, $A_3$, $A_4$, and $A_5$ is N. In an alternate embodiment of the compound described above, two of $A_1$, $A_2$, $A_3$, $A_4$, and $A_5$ are N.

According to one embodiment of the compound described above, $A_1$ is N. In some embodiments of the compound described above, $A_2$ is N. In another embodiment of the compound described above, $A_3$ is N.

According to another embodiment of the compound described above, at least one of $A_1$, $A_2$, $A_3$, $A_4$, and $A_5$ is $CR^1$. In a preferred embodiment of the compound described above, one of $A_1$, $A_2$, $A_3$, $A_4$, and $A_5$ is $CR^1$. In an alternate embodiment of the compound described above, two of $A_1$, $A_2$, $A_3$, $A_4$, and $A_5$ are $CR^1$.

According to one embodiment of the compound described above, $A_1$ is $CR^1$. In some embodiments of the compound described above, $A_2$ is $CR^1$. In another embodiment of the compound described above, $A_3$ is $CR^1$.

In one embodiment of the compound described above, $A_2$ is N and $A_3$ is $CR^1$. In another embodiment of the compound described above, $A_2$ is $CR^1$ and $A_3$ is N.

According to an embodiment of the compound described above, $Z_1$ and $Z_2$ are CH. According to an alternative embodiment of the compound described above, $Z_1$ is N and $Z_2$ is CH. According to another alternative embodiment of the compound described above, $Z_1$ is CH and $Z_2$ is N.

Pharmaceutical Compositions

The present disclosure also relates to a pharmaceutical composition comprising physiologically acceptable surface active agents, carriers, diluents, excipients, smoothing agents, suspension agents, film forming substances, and coating assistants, or a combination thereof; and a compound of Formula (I) as disclosed herein. The compound of Formula (I) included in the pharmaceutical composition may also be any compound of the preferred embodiments described above. Acceptable carriers or diluents, as well as other additives to be combined with a compound of Formula (I) as disclosed herein to provide a pharmaceutical composition, for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions described herein can be administered to a human patient per se, or in pharmaceutical compositions where they are mixed with other active ingredients, as in combination therapy, or suitable carriers or excipient(s). Examples of active ingredients include Incretin mimetics, Metformins, PPAR agonists, sulfonylureas, insulin and insulin formulations, SGLT inhibitors, glucokinase activators, and bile acid receptor agonists. Techniques for formulation and administration of the compounds of the instant application may be found in "Remington's Pharmaceutical Sciences," Mack Publishing Co., Easton, Pa., 18th edition, 1990.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Additional therapeutic or diagnostic agents may be incorporated into the pharmaceutical compositions. Alternatively or additionally, pharmaceutical compositions may be combined with other compositions that contain other therapeutic or diagnostic agents.

Uses

The compounds of Formula (I) or pharmaceutical compositions disclosed herein may be used in therapy, such as for use in treating diabetes, preferably type-2 diabetes. The compounds of Formula (I) or pharmaceutical compositions disclosed herein may also be used in treatment of disorders and diseases, where the function or dysfunction of AQP9 contributes to the development or maintenance of disease, such as diabetes, atherosclerosis, disuse osteoporosis, non-alcoholic fatty liver disease, acute kidney injury, kidney ischemia-reperfusion injury, inflammatory diseases e.g. inflammatory bowel disease, psoriasis, allergic contact dermatitis or rheumatoid arthritis. The compounds of Formula (I) or pharmaceutical compositions disclosed herein may also be used in a medicament. The compounds of Formula (I) or pharmaceutical compositions disclosed herein may also be used to modulate the activity of an aquaporin 9 protein. Preferably, modulating the activity of an aquaporin 9 protein comprises inhibiting the activity of the aquaporin 9 protein. In a preferred embodiment, the use of the compounds of Formula (I) or pharmaceutical compositions disclosed herein to modulate the activity of an aquaporin 9 protein is a non-therapeutic use. The compound of Formula (I) or pharmaceutical composition that is used in any of the described therapies (such as for use in treating diabetes), or used in treatment of disorders and diseases where the function or dysfunction of AQP9 contributes to the development or maintenance of disease, or used in a medicament, or used for modulating the activity of an aquaporin 9 protein (e.g. in a non-therapeutic use) may also be any compound or pharmaceutical composition of the preferred embodiments described above. Alternatively, the compound of Formula (I) that is used in any of the described therapies (such as for use in treating diabetes), or used in treatment of disorders and diseases where the function or dysfunction of AQP9 contributes to the development or maintenance of disease, or used in a medicament, or used for modulating the activity of an aquaporin 9 protein (e.g. in a non-therapeutic use) may be a compound selected from the group consisting of:

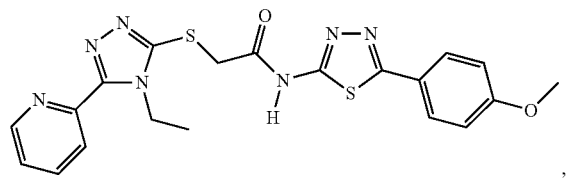

,

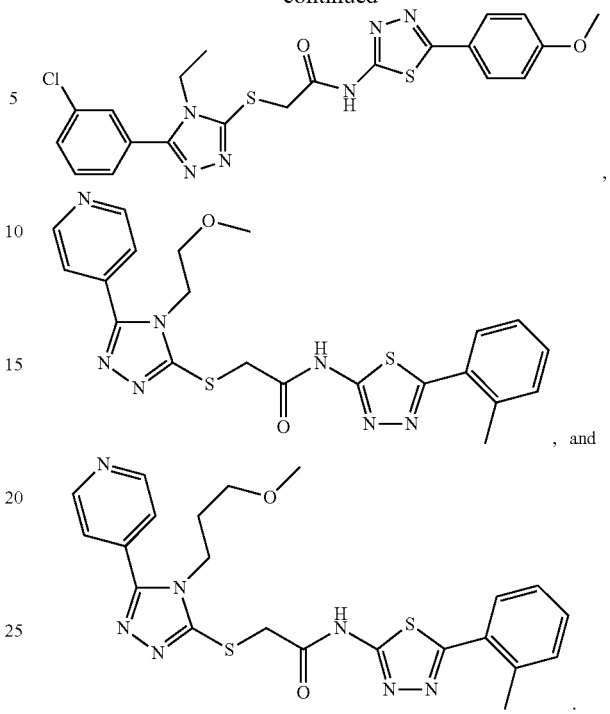

, and

Methods of Administration

The compounds or pharmaceutical compositions may be administered to the patient by any suitable means including though oral pathways such as administration in a capsule, tablet, granule, spray, syrup, or other such forms. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. Determination of a therapeutically effective amount is well within the capability of those skilled in the art, especially in light of the detailed disclosure provided herein.

Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In cases of administration of a pharmaceutically acceptable salt, dosages may be calculated as the free base. In some embodiments, the composition is administered 1 to 4 times per day. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using a MEC value. Compositions should be administered using a regimen which maintains plasma levels above the MEC for 10-90% of the time, preferably between 30-90% and most preferably between 50-90%.

The compounds or pharmaceutical compositions disclosed herein may be administered to the patient alone or in combination with other therapeutic agents against type 2 diabetes. Examples of of such therapeutic agents are current anti-type 2 diabetic therapies such as Incretin mimetics, Metformins, PPAR agonists, sulfonylureas as well as insulin. Additional examples include newer anti-type 2 diabetic drugs such as SGLT inhibitors, glucokinase activators, novel insulin formulations, and bile acid receptor agonists. The therapeutic agents may be administered simultaneously with the compounds or pharmaceutical compositions disclosed herein. Alternatively, the therapeutic agents may be administered sequentially with the compounds or pharmaceutical compositions disclosed herein. The dosage amount and interval between administration of the compounds and therapeutic agents may be adjusted as described immediately above.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to metabolic diseases, inflammatory diseases, cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

General Remarks

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality.

EXPERIMENTAL

The following examples are mere examples and should by no mean be interpreted to limit the scope of the invention. Rather, the invention is limited only by the accompanying claims.

General Chemical Procedures

Nuclear Magnetic Resonance (NMR) spectra were recorded on a Varian instrument at 400 MHz and 25° C. Chemical shifts are reported in ppm (δ) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet.

LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength: 254 nm.

Preparative HPLC were performed on a Gilson system. Flow: 10 ml/min Column: kromasil 100-5-C18 column. Wavelength: 254 nm. Solvent A water+0.1% TFA and solvent B Acetonitrile+0.1% TFA. Gradient: 40% to 95% B in 15 min.

All commercial reagents were used as received.
The following abbreviations are used herein.
Aq. Aqueous solution
ACN Acetonitrile
$CH_3CN$ Acetonitrile
$CDCl_3$ Chloroform-d
DIEA N,N-Diisopropylethylamine
DCC N,N'-Dicyclohexylcarbodiimide
DCM Dichloromethane
DMF N,N-dimethylformamide
DMSO-$d_6$ Dimethylsulfoxide-d6
EDC N-(3-Dimethylaminopropyl)-N'-ethylcarbodiimide
EtOAc Ethylacetate
HCl Hydrochloric acid
$H_2O$ Water
HPLC High Performance Liquid Chromatography HATU N-[(Dimethylamino)-1H-1,2,3-triazolo-[4,5-b]pyridin-1-ylmethylene]-N-methylmethanaminium hexafluorophosphate N-oxide
HOAT 1-Hydroxy-7-azabenzotriazole
KOH Potassium hydroxide
LC-MS Liquid Chromatography with Mass Spectrographic detection
LiOH Lithium hydroxide
Mesyl Chloride Methyl sulfonyl chloride
MeOH Methanol
$MgSO_4$ Magnesium Sulfate
$NaHCO_3$ Sodium bicarbonate
$Na_2SO_4$ Sodium Sulfate
NaOH Sodium hydroxide
NMR Nuclear Magnetic Resonance spectrometry
$POCl_3$ Phosphorus(V) oxychloride
RT Room Temperature
TFA Trifluoroacetic Acid
THF Tetrahydrofuran
$NEt_3$ Triethylamine
TEA Triethylamine Synthetic Procedures Synthesis of Intermediates 1 to 46.

Intermediate 1

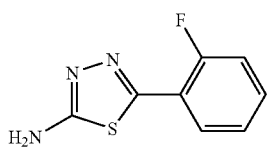 [SMILES: Nc1nnc(-c2ccccc2F)s1]

5-(2-fluorophenyl)-1,3,4-thiadiazol-2-amine

A mixture of 2-fluorobenzoic acid (3 g, 21.4 mmol) and thiosemicarbazide (1.95 g, 21.4 mmol) in $POCl_3$ (15 ml) was heated to 80° C. for 3 hours. The reaction mixture was cooled and poured into ice water and then brought to pH about 6. The water was extracted several times with EtOAc. The organic phase was washed with brine, dried ($MgSO_4$), filtered and concentrated under reduced pressure to give the title compound 3.4 g (81%).

LC-MS (ES): 196.2 (M+H), $^1$H NMR (DMSO-$d_6$) δ 8.08 (dt, 1H), 7.50 (m, 1H), 7.45 (s, 2H), 7.39 (dd, 1H), 7.34 (dq, 1H).

Intermediates 2-4 were prepared in a manner analogous to intermediate 1

Intermediate 2

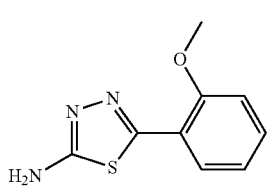

5-(2-methoxyphenyl)-1,3,4-thiadiazol-2-amine

LC-MS (ES): 208.2 (M+H), $^1$H NMR (DMSO-$d_6$) δ 7.46 (brs, 2H), 7.37 (t, 1H), 7.32-7.26 (m, 2H), 7.01 (dd, 1H), 3.81 (s, 3H).

Intermediate 3

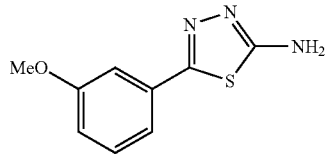 [SMILES: COc1cccc(-c2nnc(N)s2)c1]

5-(3-methoxyphenyl)-1,3,4-thiadiazol-2-amine $^1$H NMR (DMSO-$d_6$): δ 7.41 (s, 2H), 7.40-7.34 (m, 1H), 7.32-7.26 (m, 2H), 7.03-6.98 (m, 1H), 3.81 (s, 3H).

Intermediate 4

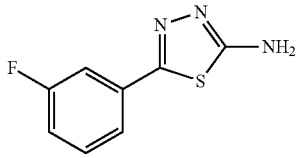 [SMILES: Nc1nnc(-c2cccc(F)c2)s1]

5-(3-Fluorophenyl)-1,3,4-thiadiazol-2-amine $^1$H NMR (DMSO-$d_6$): δ 7.65-7.59 (m, 2H), 7.57-7.50 (m, 1H), 7.36-7.30 (m, 1H)

Intermediate 5

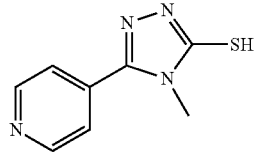

4-methyl-5-(pyridine-4-yl)-4H-1,2,4-triazole-3-thiol

Isonicotinoyl chloride hydrochloride (500 mg, 2.81 mmol) was added to a solution of 4-methyl-3-thiosemicarbazide (266 mg, 2.53 mg) and pyridine (10 ml) and the resulting solution was stirred at room temperature overnight and then the solvent was evaporated under reduced pressure. The residue was treated with an aqueous sodium hydroxide solution (50 ml, 0.5N) and the mixture was stirred at 100° C. overnight. The mixture was cooled to room temperature and the pH adjusted to pH 6 using an aqueous HCl solution (2M) and the resulting precipitate was filtered and dried in vacuum to give the title product 360 mg (67%).

LC-MS (ES): 193.2 (M+H), $^1$H NMR (DMSO-$d_6$) δ 8.79 (dd, 2H), 7.76 (dd, 2H), 3.60 (s, 3H).

Intermediate 6

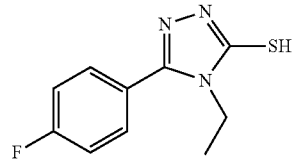

4-Ethyl-5-(4-fluorophenyl)-4H-1,2,4-triazole-3-thiol

A mixture of 4-fluorobenzoic acid (1.0 g, 7.14 mmol), hydroxybenzotriazole (0.96 g, 7.14 mmol) and diisopropylcarbodiimide (1.13 ml, 7.14 mmol) in 10 ml of DMF was stirred for 15 min. 4-Ethyl-3-thiosemicarbazide (0.88 g, 7.14 mmol) was added. The reaction mixture was stirred at RT for 48 hours. The solution was filtered and the DMF was removed under reduced pressure. The residue was dissolved in 75 ml 0.5M NaOH and heated at 100° C. for 4 hours. The solution was filtered and pH was adjusted to 6. The resulting precipitate was filtered off and washed with water and dried to give the title product (1.1 g, 69%).

LC-MS (ES): 224 (M+H), $^1$H NMR (DMSO-$d_6$) δ 7.78-7.71 (m, 2H), 7.42 (t, 2H), 4.02 (q, 2H), 1.13 (t, 3H).

Intermediate 7

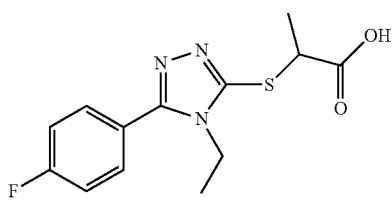 [SMILES: CCn1c(SC(C)C(=O)O)nnc1-c1ccc(F)cc1]

2-{[4-Ethyl-5-(4-fluorophenyl)-4H-1,2,4-triazole-3-yl]sulfanyl}propanoic acid

4-Ethyl-5-(4-fluorophenyl)-4H-1,2,4-triazole-3-thiol (244 mg, 1.09 mmol) was dissolved in 6 ml 0.75M KOH. 2-chloropropionic acid (151 μl, 1.64 mmol) was added and the mixture was heated to 100° C. for 6 hours. Further 50 μl 2-chloropropionic acid was added and the heating was continued for 3 hours. The reaction was acidified with 1M HCl and extracted with EtOAc. The organic phase was washed with brine, dried, filtered and concentrated under reduced pressure to give the title product (0.32 g, 100%).

LC-MS (ES): 296 (M+H), $^1$H NMR (400 MHz, DMSO-$d_6$) δ 7.79-7.66 (m, 2H), 7.41 (t, 2H), 4.25 (q, 1H), 4.03 (q, 2H), 1.54 (d, 3H), 1.18 (t, 3H).

Intermediate 8

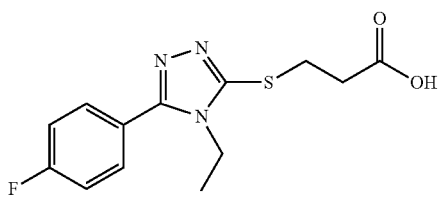 [SMILES: CCn1c(SCCC(=O)O)nnc1-c1ccc(F)cc1]

2-{[4-Ethyl-5-(4-fluorophenyl)-4H-1,2,4-triazole-3-yl]sulfanyl}propanoic acid

4-Ethyl-5-(4-fluorophenyl)-4H-1,2,4-triazole-3-thiol (193 mg, 0.86 mmol) was dissolved in 6 ml 0.75M KOH. 3-Chloropropionic acid (119 μl, 1.30 mmol) was added and the mixture was heated to 100° C. for 6 hours. Further 50 μl 3-chloropropionic acid was added and the heating was continued for 3 hours. The reaction was acidified with 1M HCl and extracted with EtOAc. The organic phase was washed with brine, dried, filtered and concentrated under reduced pressure to give the title product (0.23 g, 91%).

LC-MS (ES): 457.0 (M+H), $^1$H NMR (DMSO-$d_6$) δ 12.45 (s, 1H), 7.74-7.67 (dd, 2H), 7.40 (t, 2H), 3.95 (q, 2H), 3.35 (t, 2H), 2.77 (t, 2H), 1.18 (t, 3H).

Intermediate 9

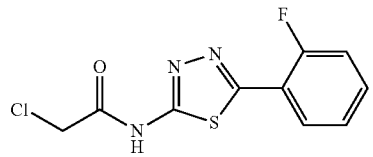 [SMILES: O=C(CCl)Nc1nnc(-c2ccccc2F)s1]

2-chloro-N-[5-(2-fluorophenyl)-1,3,4-thiadiazol-2-yl]acetamide

To a solution of 5-(2-fluorophenyl)-1,3,4-thiadiazol-2-amine (300 mg, 1.54 mmol) in THF (15 ml) and triethylamine (321 μl, 2.32 mmol) was added 2-chloroacetyl chloride (122 μl, 1.54 mmol) in THF (10 ml) drop-wise. The solution was stirred for 2 hours at RT. 25 ml of water was added and the resulting precipitate was filtered, washed with water and dried in vacuum to give the title product (193 mg, 46%). A second crop was filtered to give (88 mg, 21%).

LC-MS (ES): 272, 274 (M+H), $^1$H NMR (DMSO-$d_6$) δ 13.11 (s, 1H), 8.25 (t, 1H), 7.61 (q, 1H), 7.53-7.36 (m, 2H), 4.48 (s, 2H).

Intermediate 10

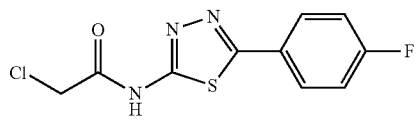 [SMILES: O=C(CCl)Nc1nnc(-c2ccc(F)cc2)s1]

2-Chloro-N-[5-(4-fluorophenyl)-1,3,4-thiadiazol-2-yl]acetamide

To a mixture of 2-amino-5-(4-fluorophenyl)-1,3,4-thiadiazole (417 mg, 2.03 mmol) and triethylamine (425 μl, 3.05 mmol) in 15 ml dioxane was added drop-wise chloroacetyl chloride (206 μl, 2.54 mmol) in 10 ml dioxane over a period of 10 min. The reaction was stirred at RT for 4 h and then poured into 75 ml of water. The resulting precipitate was filtered off and washed with water and dried to give the title product (525 mg, 95%).

LC-MS (ES): 272.1 (M+H), $^1$H NMR (DMSO-$d_6$) δ 13.05 (s, 1H), 8.02 (t, 2H), 7.38 (t, 2H), 4.48 (s, 2H).

Intermediates 11-14 were prepared in a manner analogous to intermediate 10.

Intermediate 11

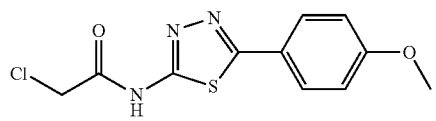 [SMILES: COc1ccc(-c2nnc(NC(=O)CCl)s2)cc1]

2-Chloro-N-[5-(4-methoxyphenyl)-1,3,4-thiadiazol-2-yl]acetamide

LC-MS (ES): 284.1 (M+H), $^1$H NMR (DMSO-$d_6$) δ 12.96 (s, 1H), 7.89 (d, 2H), 7.09 (d, 2H), 4.46 (s, 2H), 3.83 (s, 3H).

Intermediate 12

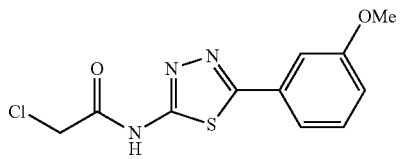 [SMILES: COc1cccc(-c2nnc(NC(=O)CCl)s2)c1]

2-chloro-N-[5-(3-methoxyphenyl)-1,3,4-thiadiazol-2-yl]acetamide $^{1}$H NMR (DMSO-d$_6$): δ 13.06 (s, 1H), 7.52-7.42 (m, 3H), 7.13-7.08 (m, 2H), 4.47 (s, 2H), 3.85 (s, 3H).

Intermediate 13

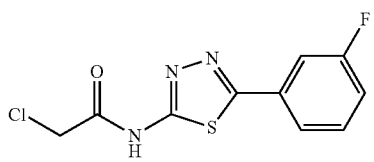 [SMILES: O=C(CCl)Nc1nnc(-c2cccc(F)c2)s1]

2-chloro-N-[5-(3-fluorophenyl)-1,3,4 thiadiazol-2-yl]acetamide $^{1}$H NMR (DMSO-d$_6$): δ 13.12 (s, 1H), 7.83-7.78 (m, 2H), 7.62-7.55 (m, 1H), 7.41-7.35 (m, 1H), 4.47 (s, 2H).

Intermediate 14

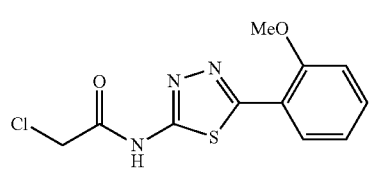 [SMILES: COc1ccccc1-c1nnc(NC(=O)CCl)s1]

2-chloro-N-[5-(2-methoxyphenyl)-1,3,4-thiadiazol-2-yl]acetamide $^{1}$H NMR (DMSO-d$_6$): δ 12.87 (s, 1H), 8.29-8.25 (m, 1H), 7.56-7.50 (m, 1H), 7.31-7.26 (m, 1H), 7.17-7.11 (m, 1H), 4.47 (s, 2H), 4.02 (s, 3H).

Intermediate 15

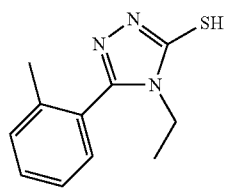

4-Ethyl-5-(2-methylphenyl)-4H-1,2,4-triazole-3-thiol

2-Methylbenzoic acid (817 mg, 6 mmol), diisopropyl carbonyldiimide (930 μl, 6 mmol) and ethyl cyano(hydroxyimino)formate (853 mg, 6 mmol) were mixed in DMF (10 ml) and stirred for 10 min. 4-Ethyl-3-thiosemicarbazide (715 mg, 6 mmol) was added and the mixture stirred overnight at RT. The mixture was filtered and the filtrate concentrated in vacuo. The residue was stirred 4 h with aq. 0.5M NaOH (60 ml) and then acidified to pH 6 with aq. 5M HCl. The precipitate was collected, washed with water and air-dried. This afforded the title intermediate (1.13 g, 86%).

$^{1}$H NMR (DMSO-d$_6$) δ 7.55-7.33 (m, 4H), 3.77 (q, 2H), 2.17 (s, 3H), 1.02 (t, 3H).

Intermediates 16-25 were prepared in a manner similar to intermediate 15.

Intermediate 16

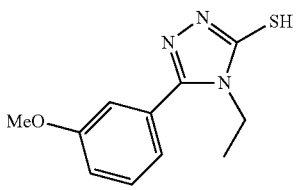 [SMILES: CCn1c(S)nnc1-c1cccc(OC)c1]

4-Ehyl-5-(3-methoxyphenyl)-4H-1,2,4-triazole-3-thiol $^{1}$H NMR (DMSO-d$_6$) δ 7.49 (t, J 1H), 7.26-7.13 (m, 3H), 4.03 (q, 2H), 3.82 (s, 3H), 1.14 (t, 3H).

Intermediate 17

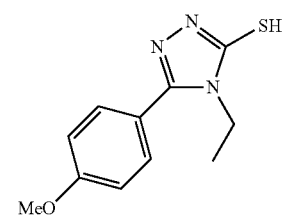 [SMILES: CCn1c(S)nnc1-c1ccc(OC)cc1]

4-Ethyl-5-(4-methoxyphenyl)-4H-1,2,4-triazole-3-thiol $^{1}$H NMR DMSO-d$_6$) δ 7.63-7.56 (m, 2H), 7.16-7.07 (m, 2H), 4.02 (q, 2H), 3.83 (s, 3H), 1.14 (t, 3H).

Intermediate 18

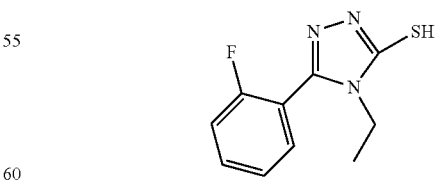

4-Ethyl-5-(2-fluorophenyl)-4H-1,2,4-triazole-3-thiol $^{1}$H NMR (DMSO-d$_6$) δ 7.79-7.61 (m, 2H), 7.54-7.37 (m, 2H), 3.85 (q, 2H), 1.08 (t, 3H).

Intermediate 19

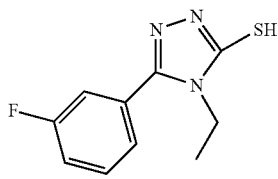

4-Ethyl-5-(3-fluorophenyl)-4H-1,2,4-triazole-3-thiol $^1$H NMR (DMSO-d$_6$) δ 7.69-7.42 (m, 4H), 4.05 (q, 2H), 1.13 (t, 3H).

Intermediate 20

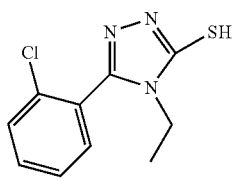

5-(2-Chlorophenyl)-4-ethyl-4H-1,2,4-triazole-3-thiol $^1$H NMR (DMSO-d$_6$) δ 7.68 (m, 3H), 7.54 (t, 1H), 3.77 (q, 2H), 1.02 (t, 3H).

Intermediate 21

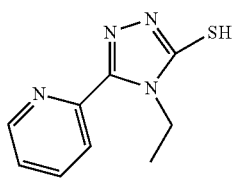

4-Ethyl-5-(pyridin-2-yl)-4H-1,2,4-triazole-3-thiol $^1$H NMR (DMSO-d$_6$) δ 8.74 (dt, 1H), 8.03-7.97 (m, 2H), 7.57 (td, 1H), 4.50 (q, 2H), 1.25 (t, 3H).

Intermediate 22

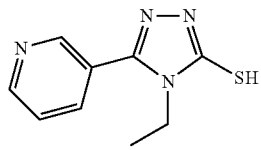

4-Ethyl-5-(pyridin-3-yl)-4H-1,2,4-triazole-3-thiol $^1$H NMR (DMSO-d$_6$) δ 8.87 (dd, 1H), 8.79 (dd, 1H), 8.14 (dt, 1H), 7.62 (ddd, 1H), 4.04 (q, 2H), 1.15 (t, 3H).

Intermediate 23

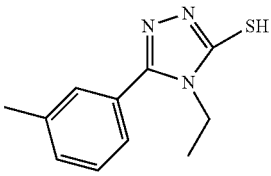

4-Ethyl-5-(3-methylphenyl)-4H-1,2,4-triazole-3-thiol $^1$H NMR (DMSO-d$_6$) δ 7.49-7.44 (m, 3H), 7.42 (dd, 1H), 4.03 (q, 2H), 2.39 (s, 3H), 1.14 (t, 3H).

Intermediate 24

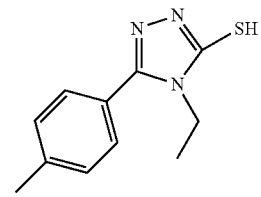

4-Ethyl-5-(4-methylphenyl)-4H-1,2,4-triazole-3-thiol $^1$H NMR (DMSO-d$_6$) δ 7.56 (d, 2H), 7.38 (d, 2H), 4.02 (q, 2H), 2.39 (s, 3H), 1.13 (t, 3H).

Intermediate 25

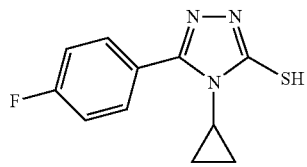 [SMILES: Fc1ccc(-c2nnc(S)n2C2CC2)cc1]

4-Cyclopropyl-5-(4-fluorophenyl)-4H-1,2,4-triazole-3-thiol $^1$H NMR (DMSO-d$_6$) δ 7.87-7.78 (m, 2H), 7.38 (t, 2H), 3.27 (t, 1H), 1.00-0.87 (m, 2H), 0.63-0.54 (m, 2H), −0.72 (s, 1H, folded).

Intermediate 26

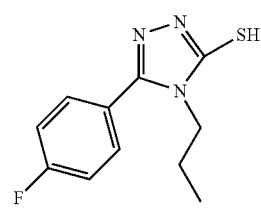 [SMILES: CCCn1c(S)nnc1-c1ccc(F)cc1]

5-(4-Fluorophenyl)-4-propyl-4H-1,2,4-triazole-3-thiol

4-Fluorobenzoic acid (420 mg, 3 mmol), diisopropyl carbonyldiimide (465 µl, 3 mmol) and hydroxybenzotriazole (454 mg, 3 mmol) were mixed in DMF (8 ml) and stirred 3 h. 4-Propyl-3-thiosemicarbazide (400 mg, 3 mmol) was added and the mixture stirred overnight. The mixture was filtered and the filtrate concentrated in vacuo. The residue was stirred with aq. 0.5M NaOH (50 ml) for 4 h at 100° C., whereupon the mixture was acidified with aq. 5M HCl to pH 6. The precipitate was collected, washed with water and air-dried to afford the title intermediate (400 mg, 56%).

$^1$H NMR (DMSO-d$_6$) δ 7.78-7.71 (m, 2H), 7.42 (t, 2H), 4.05-3.90 (m, 2H), 1.53 (h, 2H), 0.70 (t, 3H).

Intermediate 27

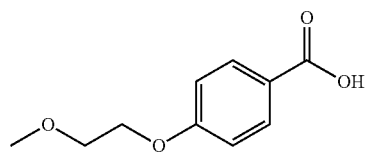

4-(2-methoxyethoxy)benzoic acid 4-hydroxybenzoic acid (2.50 g, 18.1 mmol) and KOH (2.33 g, 41.5 mmol) are dissolved in EtOH (72 ml). 1-bromo-2-methoxyethane (2.2 ml, 23.5 mmol) is added dropwise. The reaction mixture is refluxed under nitrogen for 24 hours. More KOH (2.00 g, 35.6 mmol), dissolved in EtOH (25 ml) is added to the suspension which is refluxed for another 20 h. The solvent is evaporated and, after addition of water (100 ml), the reaction mixture is acidified with HCl (5M) to pH 2.5 and extracted with ether (2×200 ml). The organic phase is dried (Na2SO4) and evaporated. 1.98 g, 55% product.

$^1$H NMR: (DMSO-d$_6$): δ 7.88 (m, 2H), 7.02 (m, 2H), 4.16 (m, 2H), 3.67 (m, 2H), 3.31 (s, 3H).

Intermediate 28

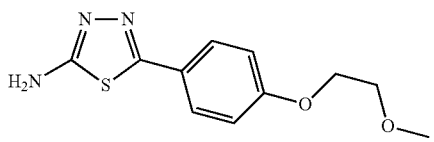 [SMILES: COCCOc1ccc(-c2nnc(N)s2)cc1]

5-[4-(2-Methoxyethoxy)phenyl]-1,3,4-thiadiazol-2-amine 4-(2-Methoxyethoxy)benzoic acid (1.18 g, 6 mmol), thiosemicarbazide (547 mg, 6 mmol) and phosphorous oxychloride (6 ml) were heated to 75° C. for 4 h under a nitrogen atmosphere. The mixture was allowed to cool and then poured onto crushed ice (40 g). This mixture was stirred overnight and then refluxed 4 h. Again the mixture was allowed to cool and then it was extracted with EtOAc. The organic phase was washed with brine and dried (Na$_2$SO$_4$). Evaporation of the solvents afforded the title intermediate (250 mg, 17%).

$^1$H NMR (DMSO-d$_6$) δ 7.71-7.62 (m, 2H), 7.27 (s, 2H), 7.05-6.98 (m, 2H), 4.17-4.10 (m, 2H), 3.71-3.64 (m, 2H), 3.35-3.28 (m, 3H).

Intermediate 29

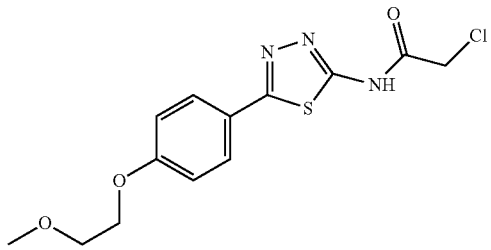 [SMILES: COCCOc1ccc(-c2nnc(NC(=O)CCl)s2)cc1]

2-Chloro-N-{5-[4-(2-methoxyethoxy)phenyl]-1,3,4-thiadiazol-2-yl}acetamide

5-[4-(2-Methoxyethoxy)phenyl]-1,3,4-thiadiazol-2-amine (199 mg, 0.8 mmol) was dissolved in THF (25 ml) and cooled on an ice/water bath. Triethylamine (175 μl, 1.3 mmol) was added followed by chloroacetyl chloride (88 μl, 1.1 mmol). After stirring this solution 2 h, water (20 ml) was added and the resulting mixture was stirred over night. A white precipitate was collected by filtration, washed with water and air dried to give the title Intermediate.

$^1$H NMR (DMSO-d$_6$) δ 12.97 (s, 1H), 7.88 (d, 2H), 7.09 (d, 2H), 4.46 (s, 2H), 4.17 (t, 2H), 3.68 (t, 2H), 3.33 (s, 3H).

Intermediate 30

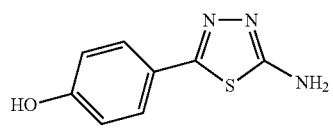 [SMILES: Nc1nnc(-c2ccc(O)cc2)s1]

4-(5-Amino-1,3,4-thiadiazol-2-yl)phenol

4-Hydroxybenzoic acid (8.287 g, 60 mmol) and thiosemicarbazide (5.468 g, 60 mmol) were heated at 75° C. in phosphorous oxychloride (70 ml, 750 mmol) overnight. The mixture was allowed to cool and then poured onto an ice/water mixture (350 g). The resulting mixture was refluxed 27 h and then allowed to cool. A precipitate was collected by filtration. This material was crystallized from isopropanol/water to afford the title intermediate (4.8 g, 41%).

$^1$H NMR (DMSO-d$_6$) δ 9.20 (bs, 1H), 7.63 (d, 2H), 6.91 (d, 2H), 6.16 (bs, 2H).

Intermediate 31

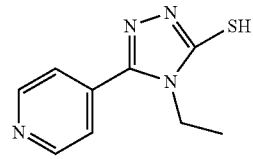

4-ethyl-5-(pyridin-4-yl)-4H-1,2,4-triazole-3-thiol

Isonicotinyl chloride (2.67 g, 15 mmol) was added to a solution of 4-ethyl-3-thiosemicarbazide (1.61 g, 13.5 mmol)

in pyridine (55 ml) and the resulting mixture was stirred 4 days. The pyridine was removed in vacuo and the residue heated at 100° C. with aq. 0.5M NaOH (150 ml) overnight. The mixture was then acidified with aq. 2M HCl. A precipitate was collected by filtration, washed with water and dried in vacuo to afford a white solid.

$^1$H NMR (DMSO-$d_6$) δ 8.83-8.76 (m, 2H), 7.75-7.69 (m, 2H), 4.10 (q, 2H), 1.18 (t, 3H).

Intermediate 32

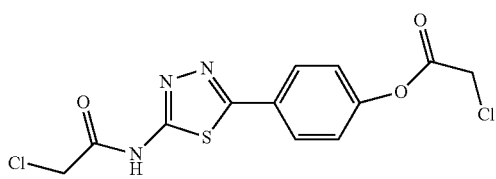 [SMILES: O=C(CCl)Nc1nnc(-c2ccc(OC(=O)CCl)cc2)s1]

5-(2-chloroacetamido)-1,3,4-thiadiazol-2-yl]phenyl 2-chloroacetate

4-[4-(5-amino-1,3,4-thiadiazol-2-yl)phenol (386 mg, 2 mmol) and NEt3 (834 µl, 6 mmol) are dissolved in THF (dry, 25 mmol) and cooled to +5° C. Chloroacetyl chloride (565 mg, 5 mmol) is added dropwise. After stirring for 1 h, the reaction mixture is poured into ice cold water (100 ml) and again stirred for 1 h. The suspension is filtered, the precipitate washed with water and air dried to give 500 mg (72%) product.

$^1$H NMR (DMSO-$d_6$): δ 13.1 (s, 1H), 8.05 (m, 2H), 7.35 (m, 2H), 4.75 (s, 2H), 4.50 (s, 2H).

Intermediate 33

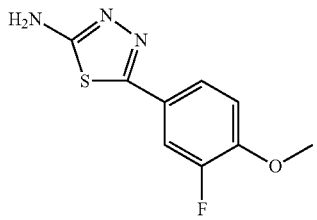

5-(3-fluoro-4-methoxyphenyl)-1,3,4-thiadiazol-2-amine

A mixture of 3-fluoro-4-methoxybenzoic acid (200 mg, 1.18 mmol) and thiosemicarbazide (107 mg, 1.18 mmol) in POCl$_3$ (1 ml) was heated to 80° C. for 45 min. The reaction mixture was cooled 5 ml of water was added slowly, Exothermic reaction. The reaction mixture was cooled and pH was adjusted to pH 7. The product was filtered and the solid was washed with water and dried to give 230 mg of the title compound as a solid.

LC-MS (ES): 226.1 (M+H), $^1$H NMR (400 MHz, DMSO-$d_6$) δ 7.64 (dd, 1H), 7.52 (d, 1H), 7.26 (q, 1H), 3.89 (s, 3H).

Intermediates 34 and 35 was prepared in a manner analogous to intermediate 33.

Intermediate 34

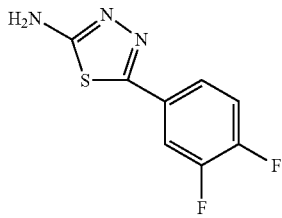 [SMILES: Nc1nnc(-c2ccc(F)c(F)c2)s1]

5-(3,4-difluorophenyl)-1,3,4-thiadiazol-2-amine

LC-MS (ES): 214.1 (M+H), $^1$H NMR (400 MHz, DMSO-$d_6$) δ 7.84 (m, 1H), 7.63-7.47 (m, 2H), 7.50 (s, 2H).

Intermediate 35

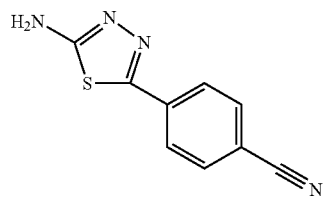 [SMILES: N#Cc1ccc(-c2nnc(N)s2)cc1]

4-(5-amino-1,3,4-thiadiazol-2-yl)benzonitrile

LC-MS (ES): 203.0 (M+H), $^1$H NMR (400 MHz, DMSO-$d_6$) δ 7.93 (dd, 4H), 7.65 (s, 2H).

Intermediate 36 and 37 was in prepared the same manner as Intermediate 15.

Intermediate 36

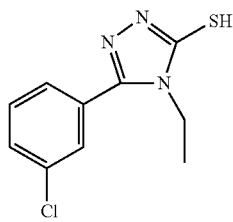

5-(3-chlorophenyl)-4-ethyl-4H-1,2,4-triazole-3-thiol $^1$H NMR (400 MHz, DMSO-$d_6$) δ 7.77 (t, 1H), 7.72-7.56 (m, 3H), 4.03 (q, 2H), 1.13 (t, 3H).

Intermediate 37

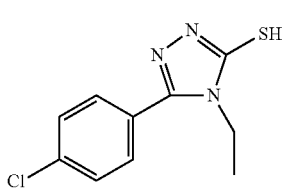

5-(4-chlorophenyl)-4-ethyl-4H-1,2,4-triazole-3-thiol $^1$H NMR (400 MHz, DMSO-$d_6$) δ 7.72 (d, 2H), 7.65 (d, 2H), 4.03 (q, 2H), 1.14 (t, 3H).

Intermediate 38 and 39 was prepared the same manner as Intermediate 1.

Intermediate 38

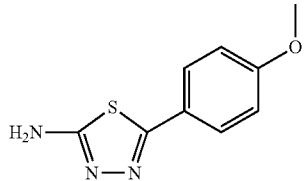

5-(4-methoxyphenyl)-1,3,4-thiadiazol-2-amine $^1$H NMR (400 MHz, DMSO-$d_6$) δ 7.68 (d, 2H), 7.28 (s, 2H), 7.28 (d, 2H), 3.80 (s, 3H).

Intermediate 39

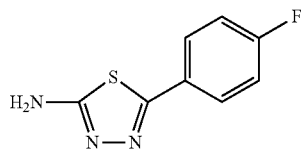 [SMILES: Nc1nnc(-c2ccc(F)cc2)s1]

5-(4-fluorophenyl)-1,3,4-thiadiazol-2-amine $^1$H NMR (400 MHz, DMSO-$d_6$) δ 7.79 (d, 2H), 7.41 (s, 1H), 7.30 (t, 2H).

Intermediate 40

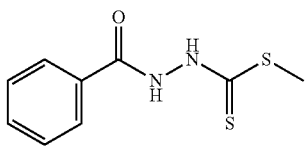

N'-[(methylsulfanyl)methanethioyl]benzohydrazide

To a Suspension of Benzhydrazide (6.8 g, 50 mmol) in MeOH (25 ml) was TEA (7 ml, 50 mmol) added. Carbon disulfide (3 ml, 50 mmol) was added dropwise at a temperature below 20° C. and was then left to stir at room temperature for 30 min. iodomethane (3.1 ml, 50 mmol) was added dropwise to the reaction and left to stir at room temperature overnight. The solution was concentrated and the product started to crystalize. The crystals was filtered off and washed with water and a small amount of MeOH to give the product. The product was recrystallized from 2-propanol to give 5 g product.

$^1$H NMR (400 MHz, DMSO-$d_6$) δ 7.89 (m, 2H), 7.68-7.56 (m, 1H), 7.59-7.47 (m, 2H), 2.48 (s, 3H).

Intermediate 41

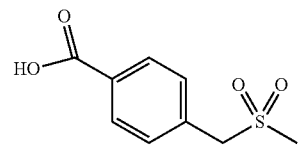

4-(methanesulfonylmethyl)benzoic acid

Methyl 4-(bromomethyl)benzoate (500 mg, 2.2 mmol) and sodium methansulfinate (445 mg, 4.4 mmol) was mixed in DMF (5 ml). The solution was heated to 70° C. for 4 hours. The reaction mixture was concentrated under reduced pressure and extracted between ethyl acetate and water. The organic layer was dried (MgSO$_4$), filtered and concentrated under reduced pressure to give 460 mg of the methylester. The methylester (1 eq) was hydrolyzed with LiOH (2 eq) in (50/50) THF/H$_2$O mixture. Upon completion of the reaction the THF was evaporated under reduced pressure and the solution was acidified with HCl to pH 2. The resulting solid was filtered to give the pure acid.

$^1$H NMR (400 MHz, DMSO-$d_6$) δ 7.96 (d, 2H), 7.53 (d, 2H), 4.59 (s, 2H), 2.93 (s, 3H).

Intermediate 42 to 44 was prepared in a manner analogous to intermediate 33.

Intermediate 42

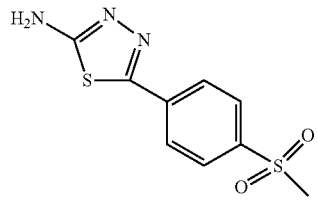 [SMILES: CS(=O)(=O)c1ccc(-c2nnc(N)s2)cc1]

5-(4-methanesulfonylphenyl)-1,3,4-thiadiazol-2-amine

LC-MS (ES): 255.9 (M+H), $^1$H NMR (400 MHz, DMSO-$d_6$) δ 8.00 (dd, 4H), 7.63 (s, 2H), 3.25 (s, 3H).

Intermediate 43

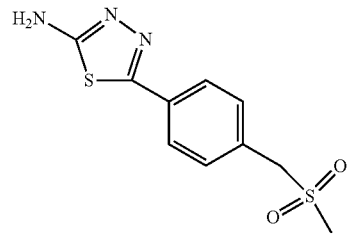 [SMILES: CS(=O)(=O)Cc1ccc(-c2nnc(N)s2)cc1]

5-[4-(methanesulfonylmethyl)phenyl]-1,3,4-thiadiazol-2-amine

LC-MS (ES): 368.3 (M+H), $^1$H NMR (400 MHz, DMSO-$d_6$) δ 7.96 (d, 2H), 7.53 (d, 2H), 4.59 (s, 2H), 2.93 (s, 3H).

Intermediate 44

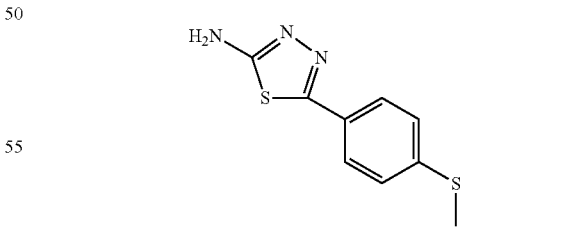

5-[4-(methylsulfanyl)phenyl]-1,3,4-thiadiazol-2-amine

LC-MS (ES): 224.0 (M+H), $^1$H NMR (400 MHz, DMSO-$d_6$) δ 7.68 (d, 2H), 7.33 (d, 2H), 2.57 (s, 3H).

Intermediates 45 and 46 were prepared in a manner analogous to intermediate 10.

Intermediate 45

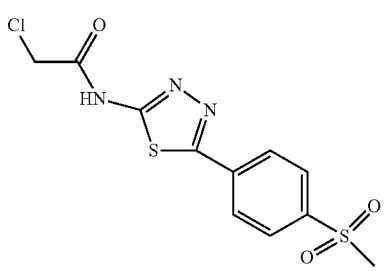 [SMILES: CS(=O)(=O)c1ccc(-c2nnc(NC(=O)CCl)s2)cc1]

2-chloro-N-[5-(4-methanesulfonylphenyl)-1,3,4-thiadiazol-2-yl]acetamide

LC-MS (ES): 332.2 (M+H), $^1$H NMR (400 MHz, DMSO-$d_6$) δ 8.24 (d, 2H), 8.07 (d, 2H), 4.50 (s, 2H), 3.29 (s, 3H).

Intermediate 46

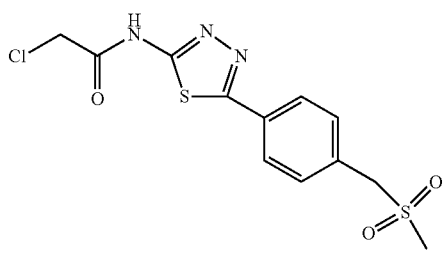 [SMILES: CS(=O)(=O)Cc1ccc(-c2nnc(NC(=O)CCl)s2)cc1]

2-chloro-N-{5-[4-(methanesulfonylmethyl)phenyl]-1,3,4-thiadiazol-2-yl}acetamide $^1$H NMR (400 MHz, DMSO-$d_6$) δ 8.00 (d, 2H), 7.57 (d, 2H), 4.59 (s, 2H), 4.47 (s, 2H), 2.94 (s, 3H).

SYNTHESIS OF EXAMPLES 1 TO 57

Example 1

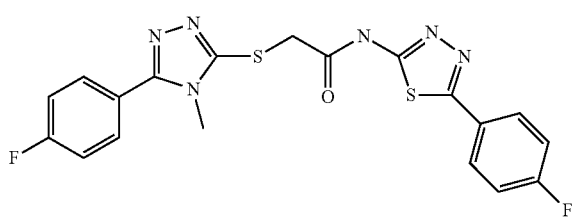 [SMILES: Cn1c(SCC(=O)Nc2nnc(-c3ccc(F)cc3)s2)nnc1-c1ccc(F)cc1]

N-[5-(4-fluorophenyl)-1,3,4-thiadizole-2-yl]-2-{[5-(4-fluorophenyl)-4-methyl-4H-1,2,4-triazole-3-yl]sulfanyl}acetamide A mixture of 4-methyl-5-(4-fluorophenyl)-4H-1,2,4-triazole-3-thiol (38 mg, 184 μmol), 1-chloro-N-[5-(4-fluorophenyl-1,3,4-thiadiazole-2-yl]acetamide (50 mg, 184 μmol) and potassium carbonate (101 mg, 734 μmol) in DMF was heated at 80° C. for 3 hours. Water was added (15 ml) and pH was adjusted to 6. The resulting precipitate was collected by centrifugation and the precipitate was washed two times with 30 ml of water. The precipitate was then dried under vacuum at 50° C. to give the title product 60 mg (74%).

LC-MS (ES): 445.0 (M+H), $^1$H NMR (400 MHz, DMSO-$d_6$) δ 13.00 (s, 1H), 8.06-7.94 (m, 2H), 7.81-7.70 (m, 2H), 7.43-7.34 (m, 4H), 4.29 (s, 2H), 3.63 (s, 3H).

Examples 2 to 22 were prepared in the same manner as example 1.

Example 2

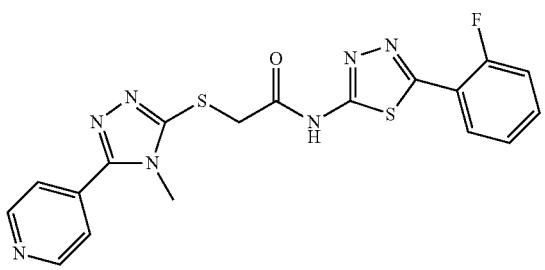 [SMILES: Cn1c(SCC(=O)Nc2nnc(-c3ccccc3F)s2)nnc1-c1ccncc1]

N-[5-(2-fluorophenyl)-1,3,4-thiadiazol-2-yl]-2-{[4-methyl-5-(pyridin-4-yl)-4H-1,2,4-triazol-3-yl]sulfanyl}acetamide Yield 15 mg. LC-MS (ES): 428.0 (M+H), $^1$H NMR (400 MHz, DMSO-$d_6$) δ 13.06 (s, 1H), 8.76 (s, 2H), 8.22 (m, 1H), 7.74 (s, 2H), 7.60 (s, 1H), 7.44 (m, 2H), 4.35 (s, 2H), 3.72 (s, 3H).

Example 3

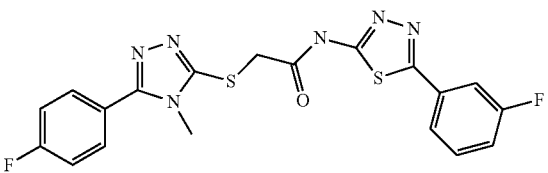 [SMILES: Cn1c(SCC(=O)Nc2nnc(-c3cccc(F)c3)s2)nnc1-c1ccc(F)cc1]

N-[5-(3-fluorophenyl)-1,3,4-thiadizole-2-yl]-2-{[5-(4-fluorophenyl)-4-methyl-4H-1,2,4-triazole-3-yl]sulfanyl}acetamide Yield 48 mg. LC-MS (ES): 445.0 (M+H), $^1$H NMR (400 MHz, DMSO-$d_6$) δ 13.09 (s, 1H), 7.83-7.71 (m, 4H), 7.58 (q, 1H), 7.39 (q, 3H), 4.30 (s, 2H), 3.63 (s, 3H).

Example 4

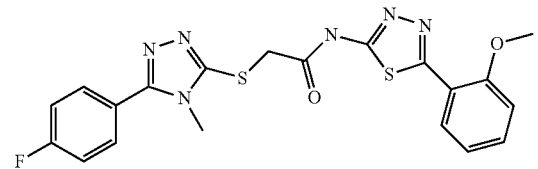 [SMILES: COc1ccccc1-c1nnc(NC(=O)CSc2nnc(-c3ccc(F)cc3)n2C)s1]

2-{[5-(4-Fluorophenyl)-4-methyl-4H-1,2,4-triazole-3-yl]sulfanyl}-N-[5-(2-methoxyphenyl)-1,3,4-thiadizole-2-yl]-acetamide Yield 57 mg. LC-MS (ES): 457.0 (M+H), $^1$H NMR (400 MHz, DMSO-$d_6$) δ 12.83 (s, 1H), 8.27 (dd, 1H), 7.76 (dd, 2H), 7.58-7.47 (dt, 1H), 7.40 (t, 2H), 7.27 (d, 1H), 7.13 (t, 1H), 4.30 (s, 2H), 3.99 (s, 3H), 3.63 (s, 3H).

Example 5

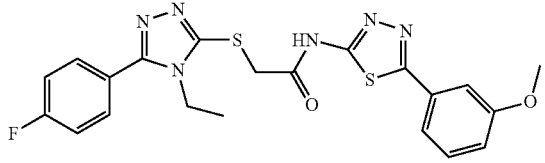 [SMILES: CCn1c(SCC(=O)Nc2nnc(-c3cccc(OC)c3)s2)nnc1-c1ccc(F)cc1]

2-{[4-ethyl-5-(4-fluorophenyl)-4H-1,2,4-triazol-3-yl]sulfanyl}-N-[5-(3-methoxyphenyl)-1,3,4-thiadiazol-2-yl]acetamide Yield 71 mg. LC-MS (ES): 471.0 (M+H), $^1$H NMR (DMSO-d$_6$) δ: 13.05 (s, 1H), 7.75-7.66 (m, 2H), 7.52-7.36 (m, 5H), 7.10 (dd, 1H), 4.35 (s, 2H), 4.02 (q, 2H), 3.84 (s, 3H), 1.23 (t, 3H).

Example 6

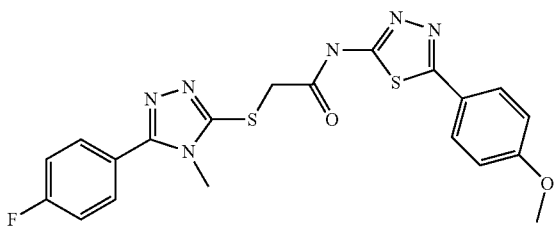 [SMILES: COc1ccc(-c2nnc(NC(=O)CSc3nnc(-c4ccc(F)cc4)n3C)s2)cc1]

2-{[5-(4-Fluorophenyl)-4-methyl-4H-1,2,4-triazole-3-yl]sulfanyl}-N-[5-(4-methoxyphenyl)-1,3,4-thiadizole-2-yl]-acetamide Yield 57 mg. LC-MS (ES): 457.0 (M+H), $^1$H NMR (400 MHz, DMSO-d$_6$) δ 12.93 (s, 1H), 7.93-7.63 (m, 4H), 7.40 (s, 2H), 7.07 (d, 2H), 4.29 (s, 2H), 3.82 (s, 3H), 3.63 (s, 3H).

Example 7

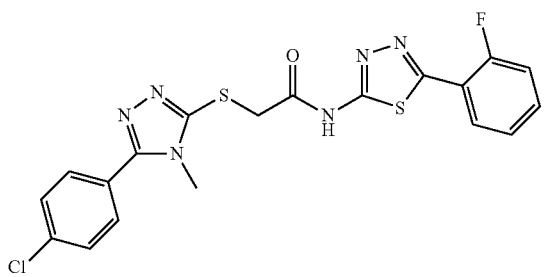 [SMILES: Cn1c(SCC(=O)Nc2nnc(-c3ccccc3F)s2)nnc1-c1ccc(Cl)cc1]

2-{[5-(4-Chlorophenyl)-4-methyl-4H-1,2,4-triazole-3-yl]sulfanyl}-N-[5-(2-fluorophenyl)-1,3,4-thiadizole-2-yl]-acetamide Yield 38 mg (64%). LC-MS (ES): 461.1, 464.1 (M+H), $^1$H NMR (400 MHz, DMSO-d$_6$) δ 8.14 (t, 1H), 7.75 (d, 2H), 7.62 (d, 2H), 7.43 (q, 1H), 7.37-7.25 (m, 2H), 3.99 (s, 2H), 3.65 (s, 3H).

Example 8

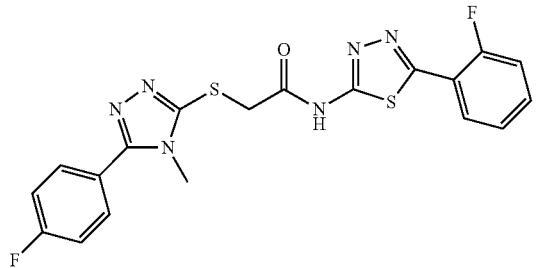 [SMILES: Cn1c(SCC(=O)Nc2nnc(-c3ccccc3F)s2)nnc1-c1ccc(F)cc1]

2-{[5-(4-Fluorophenyl)-4-methyl-4H-1,2,4-triazole-3-yl]sulfanyl}-N-[5-(2-fluorophenyl)-1,3,4-thiadizole-2-yl]-acetamide Yield 22 mg. LC-MS (ES): 445.0 (M+H), $^1$H NMR (400 MHz, DMSO-d$_6$) δ 8.24 (dt, 1H), 7.76 (dd, 2H), 7.59 (m, 1H), 7.51-7.36 (m, 4H), 4.31 (s, 2H), 3.63 (s, 3H).

Example 9

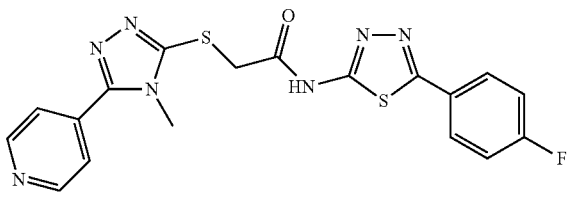 [SMILES: Cn1c(SCC(=O)Nc2nnc(-c3ccc(F)cc3)s2)nnc1-c1ccncc1]

N-[5-(4-fluorophenyl)-1,3,4-thiadiazol-2-yl]-2-{[4-methyl-5-(pyridin-4-yl)-4H-1,2,4-triazol-3-yl]sulfanyl}acetamide Yield 68 mg. LC-MS (ES): 428.0 (M+H), $^1$H NMR (400 MHz, DMSO-d$_6$) δ 13.02 (s, 1H), 8.80-8.73 (m, 2H), 8.04-7.95 (m, 2H), 7.77-7.71 (m, 2H), 7.37 (t, 2H), 4.32 (s, 2H), 3.72 (s, 3H).

Example 10

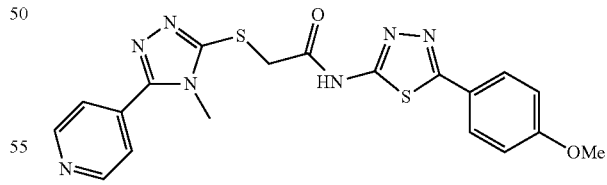

N-[5-(4-methoxyphenyl)-1,3,4-thiadiazol-2-yl]-2-{[4-methyl-5-(pyridin-4-yl)-4H-1,2,4-triazol-3-yl]sulfanyl}acetamide Yield 16 mg. LC-MS (ES): 440.0 (M+H), $^1$H NMR (400 MHz, DMSO-d$_6$) δ 8.76 (d, 2H), 7.90-7.83 (m, 2H), 7.78-7.71 (m, 2H), 7.07 (d, 2H), 4.30 (s, 2H), 3.82 (s, 3H), 3.72 (s, 3H).

Example 11

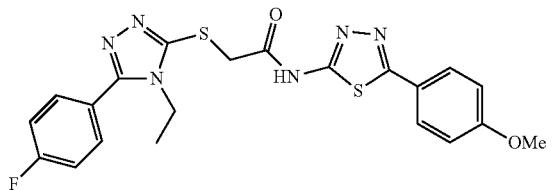 [SMILES: CCn1c(SCC(=O)Nc2nnc(-c3ccc(OC)cc3)s2)nnc1-c1ccc(F)cc1]

2-{[4-Ethyl-5-(4-fluorophenyl)-4H-1,2,4-triazol-3-yl]sulfanyl}-N-[5-(4-methoxyphenyl)-1,3,4-thiadiazol-2-yl]acetamide Yield 24 mg. LC-MS (ES): 471.1 (M+H), $^1$H NMR (400 MHz, DMSO-$d_6$) δ 7.86 (d, 2H), 7.70 (dd, 2H), 7.40 (t, 2H), 7.07 (d, 2H), 4.30 (s, 2H), 4.02 (q, 2H), 3.82 (s, 3H), 1.23 (t, 3H).

Example 12

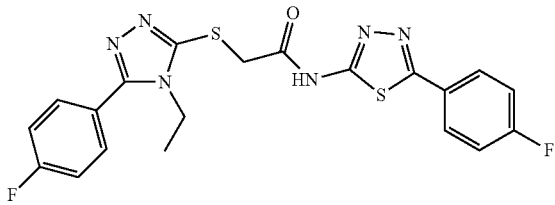 [SMILES: CCn1c(SCC(=O)Nc2nnc(-c3ccc(F)cc3)s2)nnc1-c1ccc(F)cc1]

2-{[4-Ethyl-5-(4-fluorophenyl)-4H-1,2,4-triazol-3-yl]sulfanyl}-N-[5-(4-fluorophenyl)-1,3,4-thiadiazol-2-yl]acetamide Yield 74 mg. LC-MS (ES): 459.1 (M+H), $^1$H NMR (400 MHz, DMSO-$d_6$) δ 13.05 (s, 1H), 8.04-7.96 (m, 2H), 7.70 (dd, 2H), 7.39 (dt, 4H), 4.35 (s, 2H), 4.02 (q, 2H), 1.23 (t, 3H).

Example 13

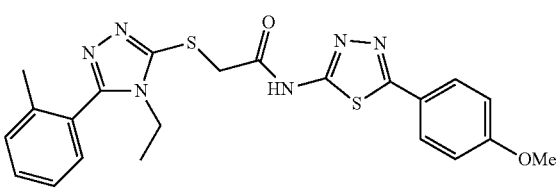 [SMILES: CCn1c(SCC(=O)Nc2nnc(-c3ccc(OC)cc3)s2)nnc1-c1ccccc1C]

2-{[4-Ethyl-5-(2-methylphenyl)-4H-1,2,4-triazol-3-yl]sulfanyl}-N-[5-(4-methoxyphenyl)-1,3,4-thiadiazol-2-yl]acetamide Yield 53 mg. LC-MS (ES): 467.0 (M+H), $^1$H NMR (400 MHz, DMSO-$d_6$) δ 12.95 (s, 1H), 7.88 (d, 2H), 7.51-7.44 (m, 1H), 7.40 (d, 1H), 7.35 (d, 2H), 7.08 (d, 2H), 4.33 (s, 2H), 3.83 (s, 3H), 3.78 (q, 2H), 2.10 (s, 3H), 1.08 (t, 3H).

Example 14

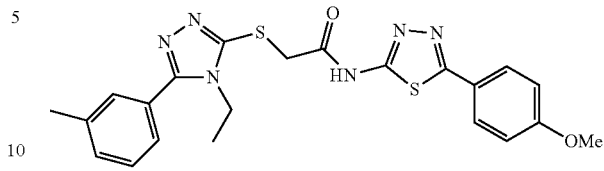

2-{[4-Ethyl-5-(3-methylphenyl)-4H-1,2,4-triazol-3-yl]sulfanyl}-N-[5-(4-methoxyphenyl)-1,3,4-thiadiazol-2-yl]acetamide Yield 68 mg. LC-MS (ES): 467.0 (M+H), $^1$H NMR (400 MHz, DMSO-$d_6$) δ 12.95 (s, 1H), 7.88 (d, 2H), 7.49-7.34 (m, 4H), 7.08 (d, 2H), 4.34 (s, 2H), 4.02 (q, 2H), 3.83 (s, 3H), 2.38 (s, 3H), 1.22 (t, 3H).

Example 15

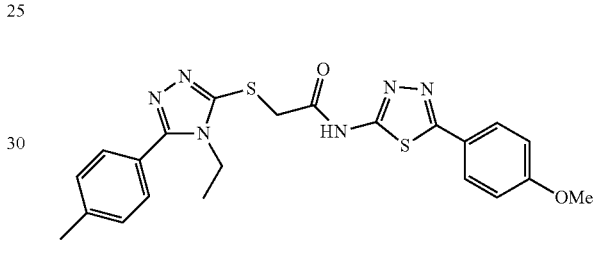

2-{[4-Ethyl-5-(4-methylphenyl)-4H-1,2,4-triazol-3-yl]sulfanyl}-N-[5-(4-methoxyphenyl)-1,3,4-thiadiazol-2-yl]acetamide Yield 63 mg. LC-MS (ES): 467.0 (M+H), $^1$H NMR (400 MHz, DMSO-$d_6$) δ 12.95 (s, 1H), 7.87 (d, 2H), 7.52 (d, 2H), 7.36 (d, 2H), 7.08 (d, 2H), 4.34 (s, 2H), 4.01 (q, 2H), 3.83 (s, 3H), 2.38 (s, 3H), 1.22 (t, 3H).

Example 16

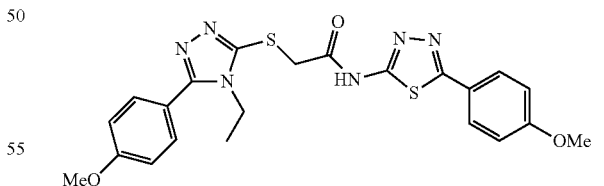

2-{[4-Ethyl-5-(4-methoxyphenyl)-4H-1,2,4-triazol-3-yl]sulfanyl}-N-[5-(4-methoxyphenyl)-1,3,4-thiadiazol-2-yl]acetamide Yield 57 mg. LC-MS (ES): 483.1 (M+H), $^1$H NMR (400 MHz, DMSO-$d_6$) δ 12.95 (s, 1H), 7.95-7.79 (m, 2H), 7.57 (d, 2H), 7.09 (t, 4H), 4.32 (s, 2H), 4.01 (q, 2H), 3.83 (s, 6H), 1.23 (t, 3H).

Example 17

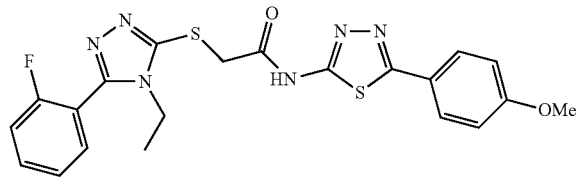

2-{[4-Ethyl-5-(2-fluorophenyl)-4H-1,2,4-triazol-3-yl]sulfanyl}-N-[5-(4-methoxyphenyl)-1,3,4-thiadiazol-2-yl]acetamide Yield 63 mg. LC-MS (ES): 471.1 (M+H), $^1$H NMR (400 MHz, DMSO-$d_6$) δ 12.97 (s, 1H), 7.88 (d, 2H), 7.67 (q, 1H), 7.58 (t, 1H), 7.50-7.36 (m, 2H), 7.08 (d, 2H), 4.37 (s, 2H), 3.88 (q, 2H), 3.83 (s, 3H), 1.17 (t, 3H).

Example 18

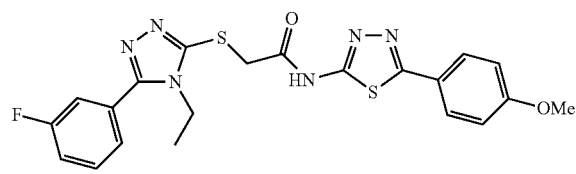 [SMILES: CCn1c(SCC(=O)Nc2nnc(-c3ccc(OC)cc3)s2)nnc1-c1cccc(F)c1]

2-{[4-Ethyl-5-(3-fluorophenyl)-1,2,4-triazol-3-yl]sulfanyl}-N-[5-(4-methoxyphenyl)-1,3,4-thiadiazol-2-yl]acetamide Yield 53 mg. LC-MS (ES): 471.1 (M+H), $^1$H NMR (400 MHz, DMSO-$d_6$) δ 12.96 (s, 1H), 7.88 (d, 2H), 7.62 (td, 1H), 7.50 (dd, 2H), 7.46-7.39 (m, 1H), 7.08 (d, 2H), 4.36 (s, 2H), 4.05 (q, 2H), 3.83 (s, 3H), 1.23 (t, 3H).

Example 19

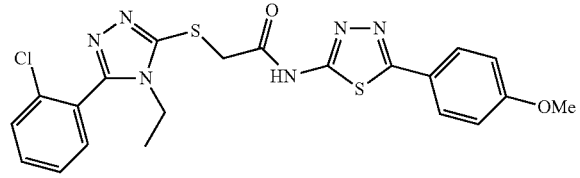 [SMILES: CCn1c(SCC(=O)Nc2nnc(-c3ccc(OC)cc3)s2)nnc1-c1ccccc1Cl]

2-{[5-(2-Chlorophenyl)-4-ethyl-4H-1,2,4-triazol-3-yl]sulfanyl}-N-[5-(4-methoxyphenyl)-1,3,4-thiadiazol-2-yl]acetamide Yield 38 mg. LC-MS (ES): 487.0 (M+H), $^1$H NMR (400 MHz, DMSO-$d_6$) δ 12.96 (s, 1H), 7.88 (d, 2H), 7.72-7.48 (m, 4H), 7.08 (d, 2H), 4.36 (s, 2H), 3.85-3.75 (m, 5H), 1.11 (t, 3H).

Example 20

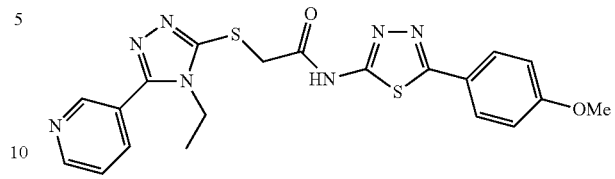

2-{[4-Ethyl-5-(pyridin-3-yl)-4H-1,2,4-triazol-3-yl]sulfanyl}-N-[5-(4-methoxyphenyl)-1,3,4-thiadiazol-2-yl]acetamide Yield 49 mg. LC-MS (ES): 454.1 (M+H), $^1$H NMR (400 MHz, DMSO-$d_6$) δ 12.96 (s, 1H), 8.85 (d, 1H), 8.79-8.72 (m, 1H), 8.13-8.06 (m, 1H), 7.88 (d, 2H), 7.60 (dd, 1H), 7.08 (d, 2H), 4.37 (s, 2H), 4.05 (q, 2H), 3.83 (s, 3H), 1.25 (t, 3H).

Example 21

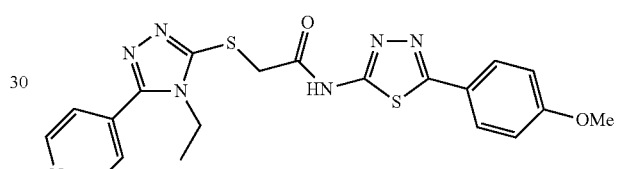

2-{[4-Ethyl-5-(pyridin-4-yl)-4H-1,2,4-triazol-3-yl]sulfanyl}-N-[5-(4-methoxyphenyl)-1,3,4-thiadiazol-2-yl]acetamide Yield 51 mg. LC-MS (ES): 454.1 (M+H), $^1$H NMR (400 MHz, DMSO-$d_6$) δ 12.96 (s, 1H), 8.77 (d, 2H), 7.87 (d, 2H), 7.69 (d, 2H), 7.07 (d, 2H), 4.38 (s, 2H), 4.12 (q, 2H), 3.82 (s, 3H), 1.27 (t, 3H).

Example 22

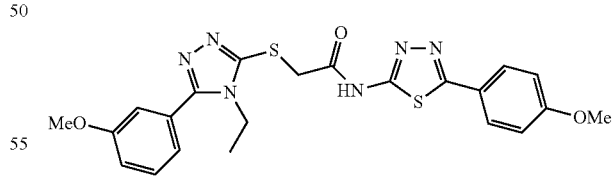

2-{[4-Ethyl-5-(3-methoxyphenyl)-4H-1,2,4-triazol-3-yl]sulfanyl}-N-[5-(4-methoxyphenyl)-1,3,4-thiadiazol-2-yl]acetamide Yield 6 mg. LC-MS (ES): 483.1 (M+H), $^1$H NMR (400 MHz, DMSO-$d_6$) δ 12.95 (s, 1H), 7.93-7.84 (m, 2H), 7.47 (t, 1H), 7.22-7.04 (m, 5H), 4.34 (s, 2H), 4.03 (q, 2H), 3.83 (s, 3H), 3.81 (s, 3H), 1.23 (t, 3H).

Example 23

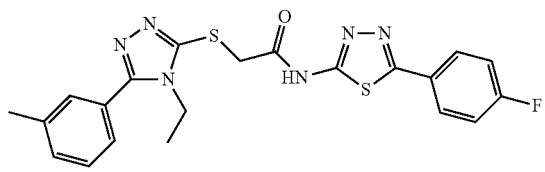 [SMILES: CCn1c(SCC(=O)Nc2nnc(-c3ccc(F)cc3)s2)nnc1-c1cccc(C)c1]

2-{[4-Ethyl-5-(3-fluorophenyl)-4H-1,2,4-triazol-3-yl]sulfanyl}-N-[5-(4-fluorophenyl)-1,3,4-thiadiazol-2-yl]acetamide 2-Chloro-N-[5-(4-fluorophenyl)-1,3,4-thiadiazol-2-yl]acetamide (54 mg, 0.2 mmol), 5-(3-methylphenyl)-4H-1,2,4-triazole-3-thiol (46 mg, 0.2 mmol) and powdered cesium carbonate (260 mg, 0.8 mmol) were mixed with DMF (2 ml) and stirred at rt 24 h. Water (10 ml) was added and the mixture was acidified to pH 5 with aq. 0.5M HCl. The precipitate was collected by filtration, washed with water and dried in vacuo at 50° C. to afford an off-white solid (42 mg).

LC-MS (ES): 455.0 (M+H), $^1$H NMR (400 MHz, DMSO-$d_6$) δ 13.04 (s, 1H), 8.01 (t, 2H), 7.55-7.26 (m, 6H), 4.35 (s, 2H), 4.02 (q, 2H), 2.38 (s, 3H), 1.22 (t, 3H).

Examples 24-33 were prepared in a manner similar to Example 23.

Example 24

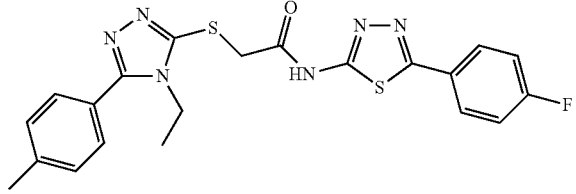 [SMILES: CCn1c(SCC(=O)Nc2nnc(-c3ccc(F)cc3)s2)nnc1-c1ccc(C)cc1]

2-{[4-Ethyl-5-(4-methylphenyl)-4H-1,2,4-triazol-3-yl]sulfanyl}-N-[5-(4-fluorophenyl)-1,3,4-thiadiazol-2-yl]acetamide Yield 37 mg. LC-MS (ES): 455.0 (M+H), $^1$H NMR (400 MHz, DMSO-$d_6$) δ 13.04 (s, 1H), 8.00 (t, 2H), 7.52 (d, 2H), 7.36 (d, 4H), 4.35 (s, 2H), 4.02 (q, 2H), 2.38 (s, 3H), 1.27-1.18 (m, 3H).

Example 25

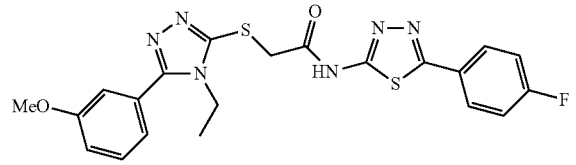 [SMILES: CCn1c(SCC(=O)Nc2nnc(-c3ccc(F)cc3)s2)nnc1-c1cccc(OC)c1]

2-{[4-Ethyl-5-(3-methoxyphenyl)-4H-1,2,4-triazol-3-yl]sulfanyl}-N-[5-(4-fluorohenyl)-1,3,4-thiadiazol-2-yl]acetamide Yield 40 mg. LC-MS (ES): 471.1 (M+H), $^1$H NMR (400 MHz, DMSO-$d_6$) δ 7.96-7.88 (m, 2H), 7.47 (t, 1H), 7.32 (t, 2H), 7.22-7.09 (m, 3H), 4.18 (s, 2H), 4.04 (q, 2H), 3.82 (s, 3H), 1.23 (t, 3H).

Example 26

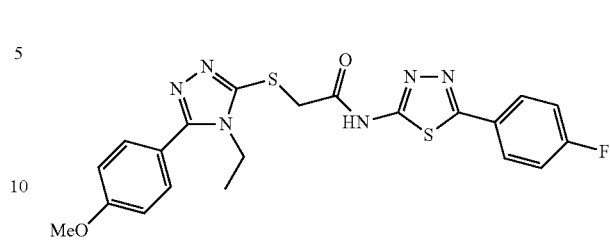

2-{[4-Ethyl-5-(4-methoxyphenyl)-4H-1,2,4-triazol-3-yl]sulfanyl}-N-[5-(4-fluorophenyl)-1,3,4-thiadiazol-2-yl]acetamide Yield 47 mg. LC-MS (ES): 453.1 (M+H), $^1$H NMR (400 MHz, DMSO-$d_6$) δ 8.01-7.93 (m, 2H), 7.57 (d, 2H), 7.35 (t, 2H), 7.10 (d, 2H), 4.26 (s, 2H), 4.01 (q, 2H), 3.83 (s, 3H), 1.23 (t, 3H).

Example 27

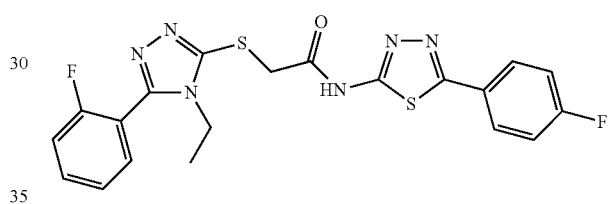

2-{[4-Ethyl-5-(2-fluorophenyl)-4H-1,2,4-triazol-3-yl]sulfanyl}-N-[5-(4-fluorophenyl)-1,3,4-thiadiazol-2-yl]acetamide Yield 59 mg. LC-MS (ES): 459.1 (M+H), $^1$H NMR (400 MHz, DMSO-$d_6$) δ 13.06 (s, 1H), 8.01 (dd, 2H), 7.67 (d, 1H), 7.58 (t, 1H), 7.42 (dt, 4H), 4.39 (s, 2H), 3.88 (q, 2H), 1.17 (t, 3H).

Example 28

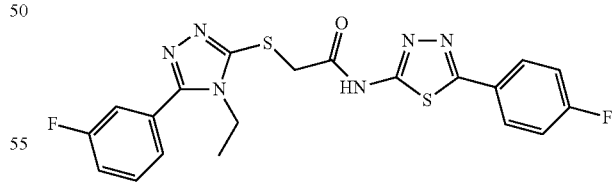

2-{[4-Ethyl-5-(3-fluorophenyl)-4H-1,2,4-triazol-3-yl]sulfanyl}-N-[5-(4-fluorophenyl)-1,2,4-thiadiazol-2-yl]acetamide Yield 55 mg. LC-MS (ES): 459.1 (M+H), $^1$H NMR (400 MHz, DMSO-$d_6$) δ 13.04 (s, 1H), 8.00 (dd, 2H), 7.62 (q, 1H), 7.54-7.46 (m, 2H), 7.40 (dt, 3H), 4.37 (s, 2H), 4.05 (q, 2H), 1.23 (t, 3H).

Example 29

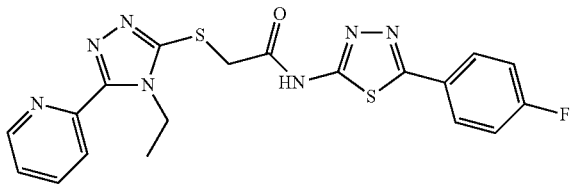 [SMILES: CCn1c(SCC(=O)Nc2nnc(-c3ccc(F)cc3)s2)nnc1-c1ccccn1]

2-{[4-Ethyl-5-(pyridin-2-yl)-4H-1,2,4-triazol-3-yl]sulfanyl}-N-[5-(4-fluorophenyl)-1,3,4-thiadiazol-2-yl]acetamide Yield 36 mg. LC-MS (ES): 442.0 (M+H), $^1$H NMR (400 MHz, DMSO-$d_6$) δ 13.04 (s, 1H), 8.72 (d, 1H), 8.11 (d, 1H), 7.99 (qd, 3H), 7.56-7.48 (m, 1H), 7.37 (t, 2H), 4.51 (q, 2H), 4.38 (s, 2H), 1.33 (t, 3H).

Example 30

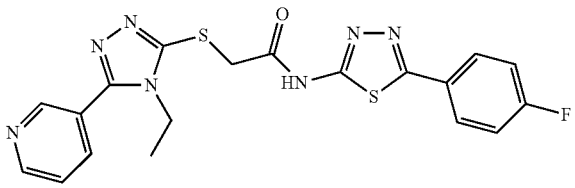 [SMILES: CCn1c(SCC(=O)Nc2nnc(-c3ccc(F)cc3)s2)nnc1-c1cccnc1]

2-{[4-Ethyl-5-(pyridin-3-yl)-4H-1,2,4-triazol-3-yl]sulfanyl}-N-[5-(4-fluorophenyl)-1,3,4-thiadiazol-2-yl]acetamide Yield 59 mg. LC-MS (ES): 442.0 (M+H), $^1$H NMR (400 MHz, DMSO-$d_6$) δ 13.05 (s, 1H), 8.85 (s, 1H), 8.75 (d, 1H), 8.09 (d, 1H), 8.00 (dd, 2H), 7.60 (dd, 1H), 7.37 (t, 2H), 4.39 (s, 2H), 4.05 (q, 2H), 1.25 (t, 3H).

Example 31

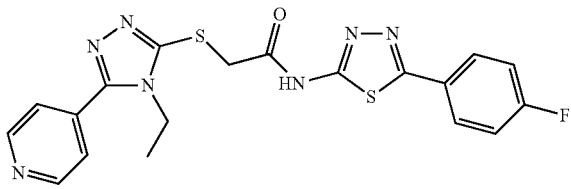 [SMILES: CCn1c(SCC(=O)Nc2nnc(-c3ccc(F)cc3)s2)nnc1-c1ccncc1]

2-{[4-Ethyl-5-(pyridin-4-yl)-4H-1,2,4-triazol-3-yl]sulfanyl}-N-[5-(4-fluorophenyl)-1,3,4-thiadiazol-2-yl]acetamide Yield 31 mg. LC-MS (ES): 442.0 (M+H), $^1$H NMR (400 MHz, DMSO-$d_6$) δ 13.05 (s, 1H), 8.77 (d, 2H), 8.00 (dd, 2H), 7.69 (d, 2H), 7.37 (t, 2H), 4.39 (s, 2H), 4.12 (q, 2H), 1.28 (t, 3H).

Example 32

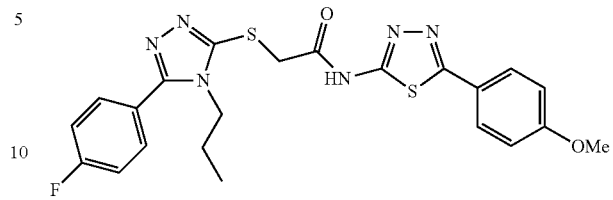

2-{[5-(4-Fluorophenyl)-4-propyl-4H-1,2,4-triazol-3-yl]sulfanyl}-N-[5-(4-methoxyphenyl)-1,3,4-thiadiazol-2-yl]acetamide Yield 57 mg. LC-MS (ES): 485.0 (M+H), $^1$H NMR (400 MHz, DMSO-$d_6$) δ 12.95 (s, 1H), 7.88 (d, 2H), 7.70 (dd, 2H), 7.40 (t, 2H), 7.08 (d, 2H), 4.35 (s, 2H), 3.96 (t, 2H), 3.83 (s, 3H), 1.58 (p, 2H), 0.72 (t, 3H).

Example 33

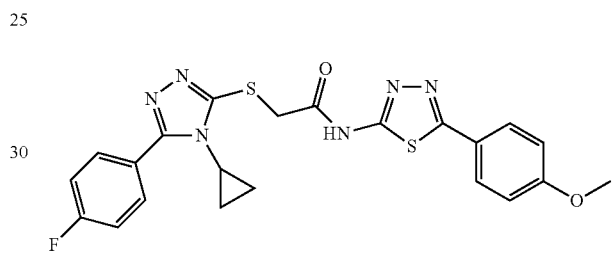

2-{[4-Cyclopropyl-5-(4-fluorophenyl)-4H-1,2,4-triazol-3-yl]sulfanyl}-N-[5-(4-methoxyphenyl)-1,3,4-thiadiazol-2-yl]acetamide Yield 70 mg. LC-MS (ES): 483.1 (M+H), $^1$H NMR (400 MHz, DMSO-$d_6$) δ 12.96 (s, 1H), 7.85 (dd, 4H), 7.37 (t, 2H), 7.08 (d, 2H), 4.40 (s, 2H), 3.83 (s, 3H), 3.54 (m, 1H), 1.04 (d, 2H), 0.66 (d, 2H).

Example 34

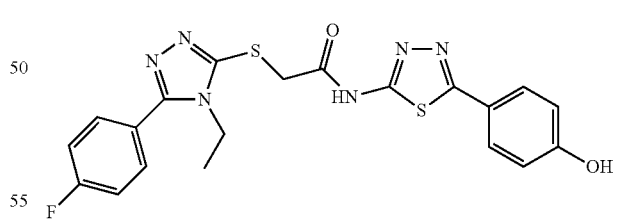

2-{[4-Ethyl-5-(4-fluorophenyl)-4H-1,2,4-triazol-3-yl]sulfanyl}-N-[5(4-hydroxyphenyl)-1,3,4-thiadiazol-2-yl]acetamide 4-(5-Amino-1,3,4-thiadiazol-2-yl)phenol (386 mg, 2 mmol) and triethylamine (834 μl, 6 mmol) were stirred in THF (25 ml). The mixture was cooled to 5° C. and chloroacetyl chloride (400 μl, 5 mmol) was added drop-wise keeping the temperature below 15° C. The mixture was stirred at 5° C. for 3 h whereupon it was poured onto water (100 ml). The resulting mixture was stirred 1 h. A precipitate was collected by filtration, washed with water and air dried to afford 4-[5-(2-chloroacetamido)-1,3,4-thiadiazol-2-yl] phenyl 2-chloroacetate (500 mg).

The crude product (242 mg, 0.7 mmol), 4-ethyl-5-(4-fluorophenyl)-4H-1,2,4-triazole-3-thiol (335 mg, 1.5 mmol) and cesium carbonate (1.63 mg, 5 mmol) were mixed in DMF (15 ml) and stirred at rt 40 h. Water (40 ml) was added and pH was adjusted to 2.5 using aq. 5M HCl. A solid was collected by filtration (160 mg). This material was dissolved in DMF (3 ml). Water (2 ml) and aq. 5M NaOH (1 ml) were added. After 3 weeks, pH was adjusted to ca 4 with aq. 1M HCl. A precipitate was collected by filtration and washed with first water and then ethanol. Air drying of this material afforded the title compound (56 mg) as an off-white powder.

LC-MS (ES): 457.0 (M+H), $^1$H NMR (400 MHz, DMSO-$d_6$) δ 12.90 (s, 1H), 10.07 (s, 1H), 7.76 (d, 2H), 7.70 (dd, 2H), 7.40 (t, 2H), 6.89 (d, 1H), 4.34 (s, 2H), 4.01 (q, 2H), 1.22 (t, 3H).

Example 35

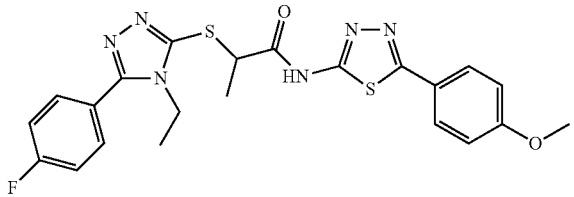 [SMILES: CCn1c(SC(C)C(=O)Nc2nnc(-c3ccc(OC)cc3)s2)nnc1-c1ccc(F)cc1]

2-{[4-Ethyl-5-(4-fluorophenyl)-4H-1,2,4-triazol-3-yl]sulfanyl}-N-[5(4-methoxyphenyl)-1,3,4-thiadiazol-2-yl]propanamide 2-{[4-Ethyl-5-(4-fluorophenyl)-4H-1,2,4-triazole-3-yl]sulfanyl}propanoic acid (41 mg, 0.2 mmol), 2-amino-5-(4-fluorophenyl)-1,3,4-thiadiazole (39 mg, 0.2 mmol), 1-ethyl-3-(3-dimethylaminopropyl)carbodiimide (46 mg, 0.24 mmol), hydroxybenzotriazole (37 mg, 0.24 mmol) and DIEA (85 μl, 0.5 mmol) were mixed in DMF (2.2 ml). The mixture was stirred overnight, diluted with water and purified by preparative HPLC. This afforded, after freeze-drying the title compound (12 mg).

LC-MS (ES): 485.0 (M+H), $^1$H NMR (400 MHz, DMSO-$d_6$) δ 12.95 (s, 1H), 7.87 (d, 2H), 7.70 (dd, 2H), 7.40 (t, 2H), 7.08 (d, 2H), 4.55 (q, 1H), 4.05-3.96 (m, 2H), 3.83 (s, 3H), 1.62 (d, 3H), 1.17 (t, 3H).

Example 36

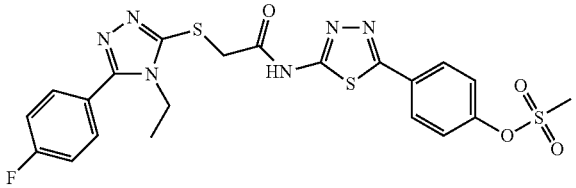 [SMILES: CCn1c(SCC(=O)Nc2nnc(-c3ccc(OS(C)(=O)=O)cc3)s2)nnc1-c1ccc(F)cc1]

4-[5-(2-{[4-Ethyl-5-(4-fluorophenyl)-4H-1,2,4-triazol-3-yl]sulfanyl}acetamido)-1,3,4-thiadiazol-2-yl] phenyl methanesulfonate 2-{[4-Ethyl-5-(4-fluorophenyl)-4H-1,2,4-triazol-3-yl] sulfanyl}-N-[5-(4-hydroxyphenyl)-1,3,4-thiadiazol-2-yl]ac-etamide (52 mg, 0.11 mmol) was dissolved in DMF (5 ml). DIEA (25 μl, 0.15 mmol) was added followed by mesyl chloride (10 μl, 0.13 mmol). The resulting mixture was stirred 6 h. More DIEA (50 μl, 0.30 mmol) and mesyl chloride (20 μl, 0.26 mmol) were added. After stirring overnight, ½ of the reaction mixture was diluted with water and purified by preparative HPLC. This afforded after freeze-drying the title compound (3 mg) as an off-white powder.

LC-MS (ES): 535.0 (M+H), $^1$H NMR (400 MHz, DMSO-$d_6$) δ 13.05 (s, 1H), 8.09-8.02 (m, 2H), 7.70 (dd, 2H), 7.55-7.47 (m, 2H), 7.40 (t, 2H), 4.34 (s, 2H), 4.02 (q, 2H), 3.45 (s, 3H), 1.23 (t, 3H).

Example 37

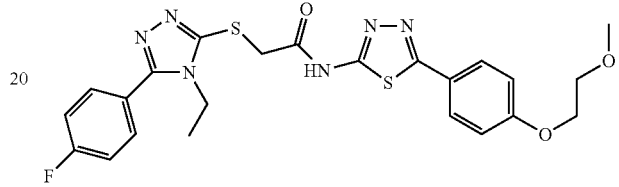

2-{[4-ethyl-5-(4-fluorophenyl)-4H-1,2,4-triazol-3-yl]sulfanyl}-N-{5-[4-(2-methoxyethoxy)phenyl]-1,3,4-thiadiazol-2-yl}acetamide 2-Chloro-N-{5-[4-(2-methoxyethoxy)phenyl]-1,3,4-thiadiazol-2-yl}acetamide (66 mg, 0.2 mmol), 4-ethyl-5-(4-fluorophenyl)-4H-1,2,4-triazole-3-thiol (46 mg, 0.21 mmol) and cesium carbonate (260 mg, 0.8 mmol) were mixed in DMF (3 ml) and stirred at rt 16 h. Water (15 ml) was added and the mixture acidified to pH 6 with aq. 5M HCl. The resulting precipitate was collected by filtration, washed with water and air-dried to afford the title compound (64 mg, 62%) as a white powder.

LC-MS (ES): 515.0 (M+H), $^1$H NMR (400 MHz, DMSO-$d_6$) δ 12.94 (s, 1H), 7.86 (d, 2H), 7.70 (dd, 2H), 7.40 (t, 2H), 7.13-7.05 (m, 2H), 4.34 (s, 2H), 4.17 (dd, 2H), 4.02 (q, 2H), 3.72-3.64 (m, 2H), 3.31 (s, 3H), 1.23 (t, 3H).

Examples 38 to 43 were prepared in the same manner as example 1.

Example 38

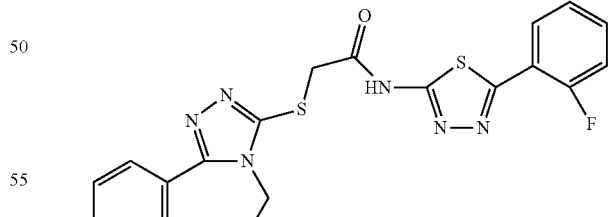

2-{[4-ethyl-5-(4-fluorophenyl)-4H-1,2,4-triazol-3-yl]sulfanyl}-N-[5-(2-fluorophenyl)-1,3,4-thiadiazol-2-yl]acetamide LC-MS (ES): 459.1 (M+H), $^1$H NMR (400 MHz, DMSO-$d_6$) δ 13.12 (s, 1H), 8.24 (td, 1H), 7.74-7.66 (m, 2H), 7.65-7.56 (m, 2H), 7.51-7.35 (m, 4H), 4.37 (s, 2H), 4.02 (q, 2H), 1.23 (t, 3H).

Example 39

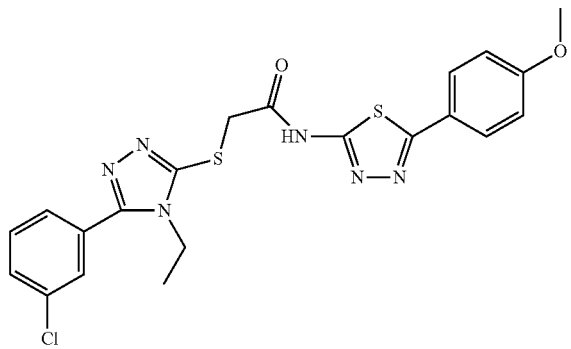 [SMILES: CCn1c(SCC(=O)Nc2nnc(-c3ccc(OC)cc3)s2)nnc1-c1cccc(Cl)c1]

2-{[5-(3-chlorophenyl)-4-ethyl-4H-1,2,4-triazol-3-yl]sulfanyl}-N-[5-(4-methoxyphenyl)-1,3,4-thiadiazol-2-yl]acetamide LC-MS (ES): 487.0 (M+H), $^1$H NMR (400 MHz, DMSO-$d_6$) δ 12.97 (s, 1H), 7.88 (d, 2H), 7.71 (s, 1H), 7.67-7.57 (m, 3H), 7.08 (d, 2H), 4.36 (s, 2H), 4.04 (q, 2H), 3.83 (s, 3H), 1.23 (t, 3H).

Example 40

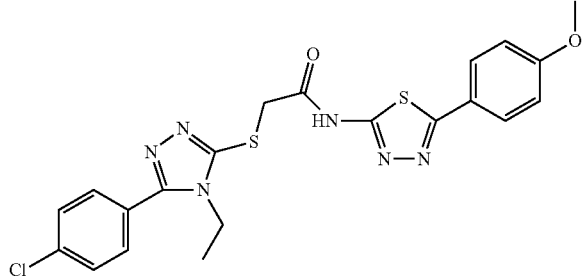 [SMILES: CCn1c(SCC(=O)Nc2nnc(-c3ccc(OC)cc3)s2)nnc1-c1ccc(Cl)cc1]

2-{[5-(4-chlorophenyl)-4-ethyl-4H-1,2,4-triazol-3-yl]sulfanyl}-N-[5-(4-methoxyphenyl)-1,3,4-thiadiazol-2-yl]acetamide LC-MS (ES): 487.0 (M+H), $^1$H NMR (400 MHz, DMSO-$d_6$) δ 7.87 (d, 2H), 7.68 (d, 2H), 7.63 (d, 2H), 7.08 (d, 2H), 4.35 (s, 2H), 4.03 (q, 2H), 3.83 (s, 3H), 1.23 (t, 3H).

Example 41

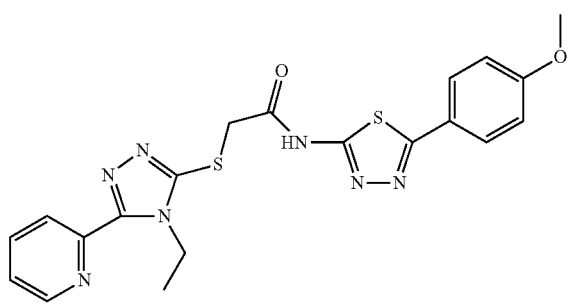 [SMILES: CCn1c(SCC(=O)Nc2nnc(-c3ccc(OC)cc3)s2)nnc1-c1ccccn1]

2-{[4-ethyl-5-(pyridin-2-yl)-4H-1,2,4-triazol-3-yl]sulfanyl}-N-[5-(4-methoxyphenyl)-1,3,4-thiadiazol-2-yl]acetamide LC-MS (ES): 454.1 (M+H), $^1$H NMR (400 MHz, DMSO-$d_6$) δ 12.97 (s, 1H), 8.71 (d, 2H), 8.11 (d, 1H), 7.98 (t, 1H), 7.87 (d, 2H), 7.51 (t, 1H), 7.07 (d, 2H), 4.51 (q, 2H), 4.37 (s, 2H), 3.82 (s, 3H), 1.32 (t, 3H).

Example 42

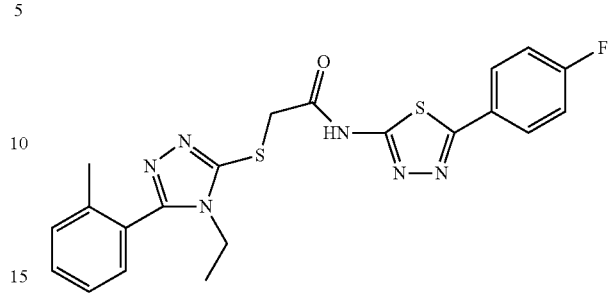

2-{[4-ethyl-5-(4-methylphenyl)-4H-1,2,4-triazol-3-yl]sulfanyl}-N-[5-(4-fluorophenyl)-1,3,4-thiadiazol-2-yl]acetamide LC-MS (ES): 455.0 (M+H), $^1$H NMR (400 MHz, DMSO-$d_6$) δ 13.05 (s, 1H), 8.01 (dd, 2H), 7.42-7.33 (m, 6H), 4.34 (s, 2H), 3.78 (q, 2H), 2.10 (s, 3H), 1.09 (t, 3H).

Example 43

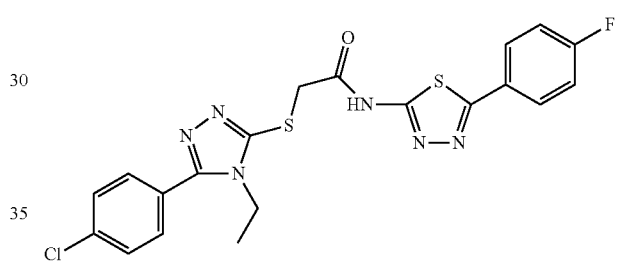

2-{[5-(4-chlorophenyl)-4-ethyl-4H-1,2,4-triazol-3-yl]sulfanyl}-N-[5-(4-fluorophenyl)-1,3,4-thiadiazol-2-yl]acetamide LC-MS (ES): 475.0 (M+H), $^1$H NMR (400 MHz, DMSO-$d_6$) δ 13.04 (s, 1H), 8.00 (dd, 2H), 7.68 (d, 2H), 6.63 (d, 2H), 7.37 (t, 2H), 4.36 (s, 2H), 4.03 (q, 2H), 1.24 (t, 3H).

Example 44

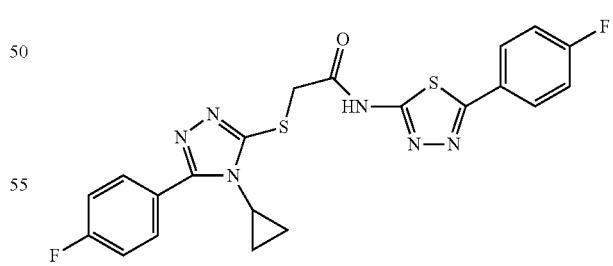

2-{[4-cyclopropyl-5-(4-fluorophenyl)-4H-1,2,4-triazol-3-yl]sulfanyl}-N-[5-(4-fluorophenyl)-1,3,4-thiadiazol-2-yl]acetamide LC-MS (ES): 471.0 (M+H), $^1$H NMR (400 MHz, DMSO-$d_6$) δ 13.06 (s, 1H), 8.00 (dd, 2H), 7.84 (dd, 2H), 7.37 (t, 4H), 4.42 (s, 2H), 3.55 (brs, 1H), 1.04 (q, 2H), 0.66 (q, 2H).

Example 45

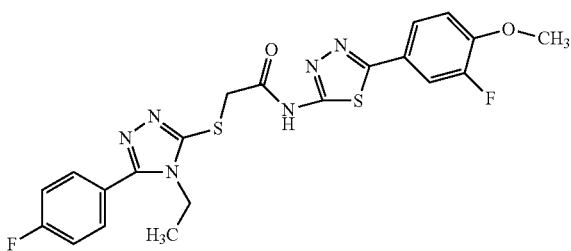 [SMILES: CCn1c(SCC(=O)Nc2nnc(-c3ccc(OC)c(F)c3)s2)nnc1-c1ccc(F)cc1]

2-{[4-ethyl-5-(4-fluorophenyl)-4H-1,2,4-triazol-3-yl]sulfanyl}-N-[5-(3-fluoro-4-methoxyphenyl)-1,3,4-thiadiazol-2-yl]acetamide To a mixture of 5-(3-fluoro-4-methoxyphenyl)-1,3,4-thiadiazol-2-amine (22.5 mg, 0.10 mmol) and triethylamine (22 µl, 0.16 mmol) in of dioxan (1 ml) was added dropwise chloroacetyl chloride (10 µl, 0.13 mmol) in dioxan (1 ml) over a period of 2 min. The reaction was stirred at room temperature for 4 hours. Potassium carbonate (55 mg, 0.40 mmol, 4-ethyl-5-(4-fluorophenyl)-4H-1,2,4-triazole-3-thiol and DMF (1 ml) was added. The mixture was heated at 80° C. for 3 hrs. The mixture was diluted with 5 ml of water and 1 ml $CH_3CN$ and purified on HPLC.

LC-MS (ES): 489.1 (M+H), $^1$H NMR (400 MHz, DMSO-$d_6$) δ 7.81 (d, 1H), 7.76-7.66 (m, 3H), 7.40 (t, 2H), 7.31 (t, 1H), 4.35 (s, 2H), 4.02 (q, 2H), 3.91 (s, 3H), 1.23 (t, 3H).

Example 46 and 47 was prepared in a manner analogous to example 45.

Example 46

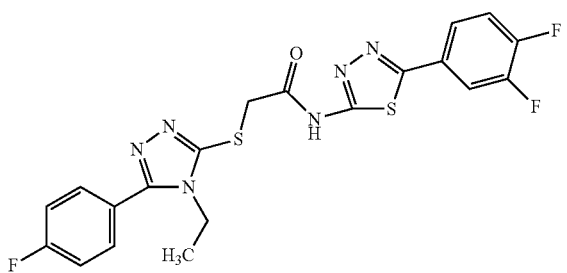 [SMILES: CCn1c(SCC(=O)Nc2nnc(-c3ccc(F)c(F)c3)s2)nnc1-c1ccc(F)cc1]

N-[5-(3,4-difluorophenyl)-1,3,4-thiadiazol-2-yl]-2-{[4-ethyl-5-(4-fluorophenyl)-4H-1,2,4-triazol-3-yl]sulfanyl}acetamide LC-MS (ES): 477.0 (M+H), $^1$H NMR (400 MHz, DMSO-$d_6$) δ 8.05 (s, 1H), 7.81 (s, 1H), 7.70 (t, 2H), 7.61 (dd, 1H), 7.40 (t, 2H), 4.37 (s, 2H), 4.02 (q, 2H), 1.23 (t, 3H).

Example 47

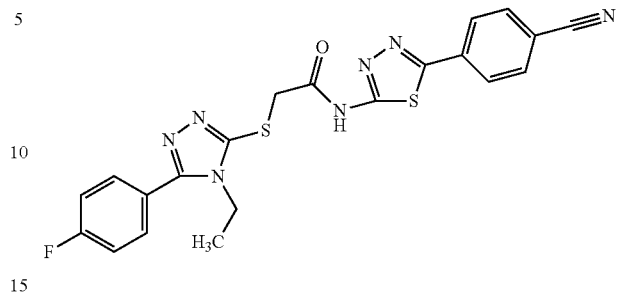

N-[5-(4-cyanophenyl)-1,3,4-thiadiazol-2-yl]-2-{[4-ethyl-5-(4-fluorophenyl)-4H-1,2,4-triazol-3-yl]sulfanyl}acetamide LC-MS (ES): 466.0 (M+H), $^1$H NMR (400 MHz, DMSO-$d_6$) δ 8.15 (d, 2H), 8.00 (d, 2H), 7.70 (dd, 2H), 7.40 (t, 2H), 4.38 (s, 2H), 4.02 (q, 2H), 1.23 (t, 3H).

Example 48

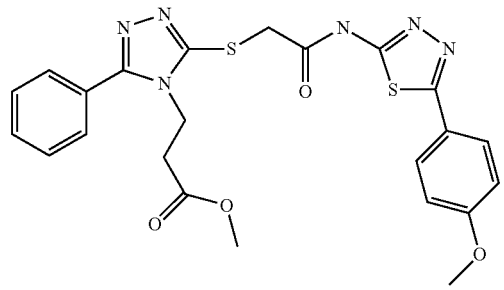 [SMILES: COC(=O)CCn1c(SCC(=O)Nc2nnc(-c3ccc(OC)cc3)s2)nnc1-c1ccccc1]

Methyl 3-{3-[({[5-(4-methoxyphenyl)-1,3,4-thiadiazol-2-yl]carbamoyl}methyl)sulfanyl]-5-phenyl-4H-1,2,4-triazol-4-yl}propanoate Step 1

A stirred mixture of 2-aminoacetamide hydrochloride (1 g, 9 mmol) and $NaHCO_3$ (3 g, 36 mmol) in dioxane:$H_2O$ (24 ml, 2:1) was added thiophosgene (0.73 ml, 9.5 mmol) at 12-16° C. and left to stir at 16° C. for 10 min. Benzydrazide (1.29 g, 9.5 mmol) was added and the mixture was left with stirring at room temperature for 2 hours. 2 ml of 1M NaOH was added and the reaction mixture was heated to 85° C. for 2 hours. The reaction mixture was cooled down and the crystals was filtered off (byproduct). The solution was acidified with HCl and the product was filtered off, washed with $H_2O$/MeOH and dried to give 700 mg product.

$^1$H NMR (400 MHz, DMSO-$d_6$) δ 13.97 (s, 1H), 7.71-7.64 (m, 2H), 7.62-7.54 (m, 3H), 4.17 (t, 2H), 2.72 (t, 2H).

Step 2

A mixture of methyl 3-(3-phenyl-5-sulfanyl-4H-1,2,4-triazol-4-yl)propanoate (100 mg, 0.4 mmol), 1-chloro-N-[5-(4-methoxyphenyl-1,3,4-thiadiazole-2-yl]acetamide (114 mg, 0.4 mmol) and TEA (48 mg, 0.47 mmol) in ACN was refluxed for 1 hour. After cooling the product was filtered off, washed with DCM and THF to give 223 mg of the crude acid.

$^1$H NMR (400 MHz, DMSO-d$_6$) δ 7.89 (d, 2H), 7.66 (m, 2H), 7.57 (m, 3H), 7.09 (d, 2H), 4.33 (s, 2H), 4.27 (t, 2H), 3.84 (s, 3H), 2.63 (t, 2H).

Step 3

To 100 mg of crude acid in MeOH (5 ml) was added 0.1 ml conc HCl. The reaction mixture was refluxed for 3 hours. Solvent was evaporated and the rest was dissolved in DCM. The DCM solution was washed with sat. NaHCO$_3$, dried over Na$_2$SO$_4$, filtered and concentrated under reduced pressure. The residue was dissolved in MeOH and left to crystalize in fridge. The product was filtered off and dried to give 50 mg.

LC-MS (ES): 511.0 (M+H), $^1$H NMR (400 MHz, DMSO-d$_6$) δ 7.89 (d, 2H), 7.63-7.63 (m, 2H), 7.62-7.5 (m, 3H), 7.09 (d, 2H), 4.35 (s, 2H). 4.32 (t, 2H). 3.84 (s, 3H). 3.49 (s, 3H). 2.71 (t, 2H).

Example 49

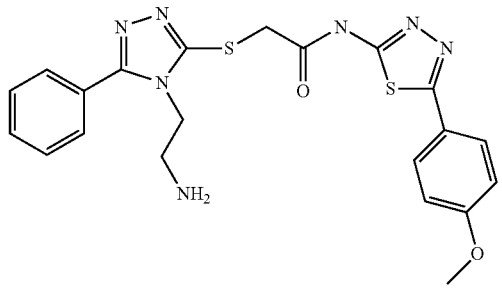

2-{[4-(2-aminoethyl)-5-phenyl-4H-1,2,4-triazol-3-yl]sulfanyl}-N-[5-(4-methoxyphenyl) 1,3,4 thiadiazol-2-yl]acetamide Step 1

1,3-dicyclohexylcarbiimide (0.64 g 3.1 mmol), carbon disulfide (1.62 g 21 mmol) and 2 mL of THF and cooled to −7 to −10° C. The tert-butyl N-(2-aminoethyl)carbamate (0.5 g, 3.1 mmol) was dissolved in 2 mL of dried THF and added dropwise to the DCC solution at −7 to −10° C. The reaction mixture was allowed to warm up to room temperature naturally and stirred at room temperature overnight. After evaporation, diethyl ether was added to the residue and the filtrate was evaporated and passed through a silica gel column with 80:20 hexanes:EtOAc to give 340 mg product $^1$H NMR (400 MHz, Chloroform-d) δ 3.66 (t, 2H), 3.39 (q, 2H), 1.47 (s, 9H).

Step 2

A solution of tert-butyl N-(2-isothiocyanatoethyl)carbamate (340 mg, 1.68 mmol) and Benzhydrazide (229 mg, 1.68 mmol) in THF (43 ml) was stirred at 50° C. for 2.5 hours. The reaction mixture was cooled down and product was filtered off, washed with a small amount of THF and dried to give 240 mg.

$^1$H NMR (400 MHz, DMSO-d$_6$) δ 10.35 (s, 1H), 9.40 (s, 1H), 8.13 (s, 1H, 7.92 (d, 2H), 7.57 (t, 1H), 7.49 (t, 2H), 3.48 (d, 2H), 3.08 (d, 2H), 1.33 (s, 9H).

Step 3 tert-butyl N-(2-{[(phenylformohydrazido)methanethioyl]amino}ethyl)carbamate (110 mg, 0.33 mmol) was mixed with NaOH (3 ml, 1M) and refluxed for 1 hour. After cooling the mixture was acidified with HCl to pH 4 and the crystals was filtered off to give 80 mg product $^1$H NMR (400 MHz, DMSO-d$_6$) δ 7.67 (d, 2H), 7.63-7.50 (m, 3H), 6.85 (t, 1H), 4.07 (t, 2H), 3.21 (q, 2H), 1.28 (s, 9H).

Step 4

A mixture of tert-butyl N-[2-(3-phenyl-5-sulfanyl-4H-1,2,4-triazol-4-yl)ethyl]carbamate (80 mg, 0.25 mmol), 1-chloro-N-[5-(4-methoxyphenyl-1,3,4-thiadiazole-2-yl]acetamide (71 mg, 0.26 mmol) and TEA (30 mg, 0.2 mmol) in ACN was refluxed for 1 hour. After cooling the product was filtered off, washed with DCM to give 100 mg.

Water was added (15 ml) and pH was adjusted to 6. The resulting precipitate was collected by centrifugation and the precipitate was washed two times with 30 ml of water. The precipitate was then dried under vacuum at 50° C. to give the title product 60 mg (74%).

$^1$H NMR (400 MHz, DMSO-d$_6$) δ 7.89 (d, 2H), 7.70-7.63 (m, 2H), 7.59-7.52 (m, 3H), 7.09 (d, 2H), 7.00 (t, 1H), 4.34 (s, 2H), 4.07 (t, 2H), 3.84 (s, 3H), 3.13 (d, 2H), 1.32 (s, 9H).

Step 5 tert-butyl N-(2-{3-[({[5-(4-methoxyphenyl)-1,3,4-thiadiazol-2-yl]carbamoyl}methyl)sulfanyl]-5-phenyl-4H-1,2,4-triazol-4-yl}ethyl)carbamate (60 mg, 0.1 mmol) was mixed with HCl (4 ml 6M). and was stirred at room temperature for 3 hours. The acidic water was washed with DCM and the organic layer was separated. The solution was basified to pH 8 and the product was filtered off, the solid was washed with MeOH and dried to give 36 mg product.

LC-MS (ES): 468.1 (M+H), $^1$H NMR (400 MHz, DMSO-d$_6$) δ 7.84 (d, 2H), 7.70-7.62 (m, 2H), 7.59-7.50 (m, 3H), 7.06 (d, 2H), 4.23 (s, 2H), 4.13 (t, 2H), 3.82 (s, 3H), 2.88 (t, 2H).

Example 50

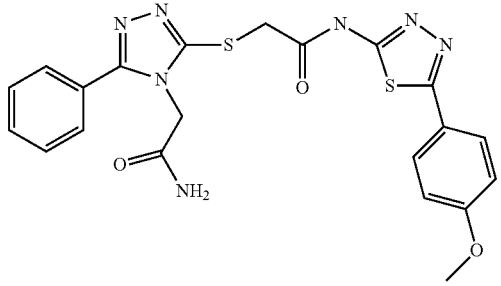 [SMILES: COc1ccc(-c2nnc(NC(=O)CSc3nnc(-c4ccccc4)n3CC(N)=O)s2)cc1]

2-{[4-(carbamoylmethyl)-5-phenyl-4H-1,2,4-triazol-3-yl]sulfanyl}-N-[5-(4methoxyphenyl)-1,3,4-thiadiazol-2-yl]acetamide Step 1

To a stirred mixture of 2-aminoacetamide hydrochloride (1 g, 9 mmol) and NaHCO$_3$ (3 g, 36 mmol) in dioxane:H$_2$O (24 ml, 2:1) was added thiophosgene (0.73 ml, 9.5 mmol) at 12-16° C. and left to stir at 16° C. for 10 min. Benzydrazide (1.29 g, 9.5 mmol) was added and the mixture was left with stirring at room temperature for 2 hours. 2 ml of 1M NaOH was added and the reaction mixture was heated to 85° C. for 2 hours. The reaction mixture was cooled down and the crystals were filtered off (byproduct). The solution was acidified with HCl and the product was filtered off, washed with H$_2$O/MeOH and dried to give 700 mg product.

$^1$H NMR (400 MHz, DMSO-d$_6$) δ 13.97 (s, 1H), 7.72 (s, 1H), 7.69-7.61 (m, 2H), 7.61-7.47 (m, 3H), 7.28 (s, 1H), 4.66 (s, 2H).

Step 2

A mixture of 2-(3-phenyl-5-sulfanyl-4H-1,2,4-triazol-4-yl)acetamide (100 mg, 0.42 mmol), 1-chloro-N-[5-(4- methoxyphenyl-1,3,4-thiadiazole-2-yl]acetamide (120 mg, 0.42 mmol) and TEA (50 mg, 0.51 mmol) in ACN (5 ml) was refluxed for 4 hour. After cooling the product was filtered off, washed with DCM to give 156 mg.

LC-MS (ES): 482.0 (M+H), $^1$H NMR (400 MHz, DMSO-$d_6$) δ 7.88 (d, 2H), 7.85 (s, 1H), 7.56 (s, 5H), 7.49 (s, 1H), 7.09 (d, 2H), 4.65 (s, 2H), 4.27 (s, 2H), 3.84 (s, 3H).

Example 51

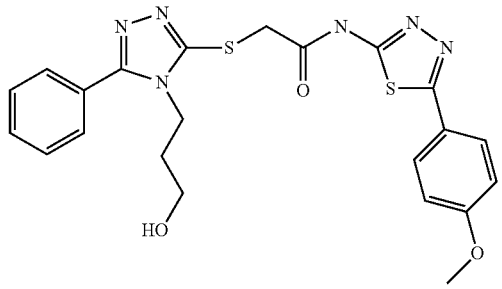 [SMILES: COc1ccc(-c2nnc(NC(=O)CSc3nnc(-c4ccccc4)n3CCCO)s2)cc1]

2-{[4-(3-hydroxypropyl)-5-phenyl-4H-1,2,4-triazol-3-yl]sulfanyl}-N-[5-(4-methoxyphenyl)-1,3,4-thiadiazol-2-yl]acetamide Step 1

N'-[(methylsulfanyl)methanethioyl]benzohydrazide (0.5 g, 2.2 mmol) was stirred with 3-aminopropanol (0.4 g, 6.6 mmol) at 110° C. for 3 hours. After cooling down 10 ml of water was added and the pH was adjusted to 1. The crystals was filtered off and dried to give 93 mg product.

$^1$H NMR (400 MHz, DMSO-$d_6$) δ 13.94 (s, 1H), 7.73-7.64 (m, 2H), 7.68-7.50 (m, 3H), 4.08 (t, 2H), 3.33 (t, 2H), 1.73 (m, 2H).

Step 2

A mixture of 2-(3-phenyl-5-sulfanyl-4H-1,2,4-triazol-4-yl)propan-1-ol (93 mg, 0.39 mmol), 1-chloro-N-[5-(4-methoxyphenyl-1,3,4-thiadiazole-2-yl]acetamide (112 mg, 0.39 mmol) and TEA (48 mg, 0.47 mmol) in ACN (5 ml) was refluxed for 4 hour. After cooling the product was filtered off, washed with DCM and H2O to give 92 mg product.

LC-MS (ES): 483.1 (M+H), $^1$H NMR (400 MHz, DMSO-$d_6$) δ 7.89 (d, 2H), 7.71-7.64 (m, 2H), 7.60-7.53 (m, 3H), 7.09 (d, 2H), 4.37 (s, 2H), 4.10 (t, 2H), 3.83 (s, 3H), 3.35 (t, 2H), 1.76 (m, 2H).

Example 52

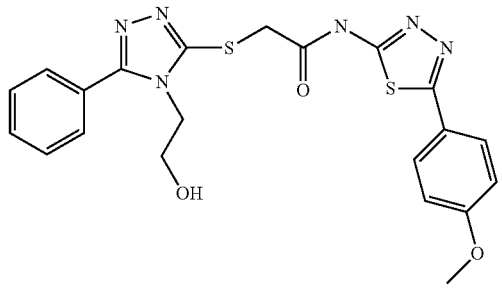 [SMILES: COc1ccc(-c2nnc(NC(=O)CSc3nnc(-c4ccccc4)n3CCO)s2)cc1]

2-{[4-(3-hydroxyethyl)-5-phenyl-4H-1,2,4-triazol-3-yl]sulfanyl}-N-[5-(4-methoxyphenyl)-1,3,4-thiadiazol-2-yl]acetamide Step 1

N'-[(methylsulfanyl)methanethioyl]benzohydrazide (0.5 g, 2.2 mmol) was stirred with 2-aminoethanol (0.4 g, 6.6 mmol) at 110° C. for 3 hours. After cooling down 10 ml of water was added and the pH was adjusted to 2. The crystals was filtered off and dried to give 195 mg product.

$^1$H NMR (400 MHz, DMSO-$d_6$) δ 13.93 (s, 1H), 7.83-7.72 (m, 2H), 7.63-7.50 (m, 3H), 5.00 (t, 1H), 4.04 (t, 2H), 3.75-3.68 (m, 2H).

Step 2

A mixture of 2-(3-phenyl-5-sulfanyl-4H-1,2,4-triazol-4-yl)ethan-1-ol (100 mg, 0.45 mmol), 1-chloro-N-[5-(4-methoxyphenyl-1,3,4-thiadiazole-2-yl]acetamide (128 mg, 0.45 mmol) and TEA (5 mg, 0.54 mmol) in ACN (5 ml) was refluxed for 4 hour. After cooling the product was filtered off, washed with DCM and H2O to give 97 mg product LC-MS (ES): 469.0 (M+H), $^1$H NMR (400 MHz, DMSO-$d_6$) δ 7.88 (d, 2H), 7.73 (dd, 2H), 7.58-7.52 (m, 3H), 7.08 (d, 2H), 4.34 (s, 2H), 4.08 (t, 2H), 3.83 (s, 3H), 3.65-3.58 (m, 4H).

Examples 53 to 57 were prepared in a manner analogous to example 45.

Example 53

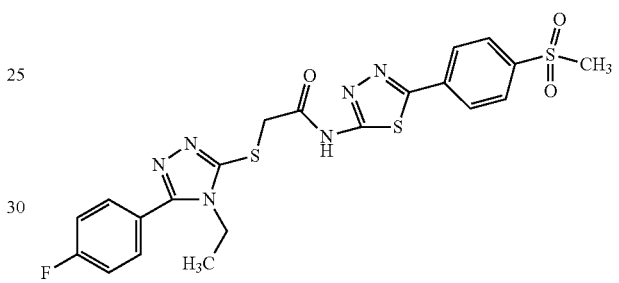

2-{[4-ethyl-5-(4-fluorophenyl)-4H-1,2,4-triazol-3-yl]sulfanyl}-N-[5-(4-methanesulfonylphenyl)-1,3,4-thiadiazol-2-yl]acetamide LC-MS (ES): 519.1 (M+H), $^1$H NMR (400 MHz, DMSO-$d_6$) δ 8.22 (d, 2H), 8.06 (d, 2H), 7.70 (dd, 2H), 7.40 (t, 2H), 4.38 (s, 2H), 4.02 (q, 2H), 3.28 (s, 3H), 1.23 (t, 3H).

Example 54

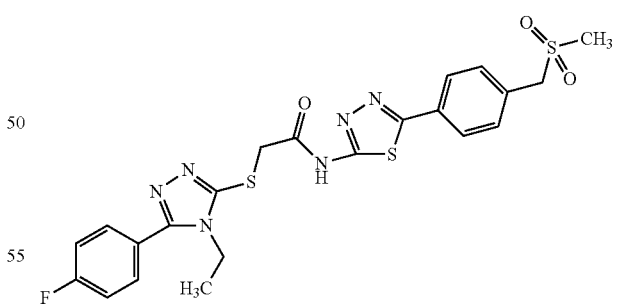

2-{[4-ethyl-5-(4-fluorophenyl)-4H-1,2,4-triazol-3-yl]sulfanyl}-N-{5-[4-(methanesulfonylmethyl)phenyl]-1,3,4-thiadiazol-2-yl}acetamide LC-MS (ES): 533.0 (M+H), $^1$H NMR (400 MHz, DMSO-$d_6$) δ 7.99 (d, 2H), 7.70 (dd, 2H), 7.56 (d, 2H), 7.40 (t, 2H), 4.58 (s, 2H), 4.37 (s, 2H), 4.02 (q, 2H), 2.94 (s, 3H), 1.23 (t, 3H).

Example 55

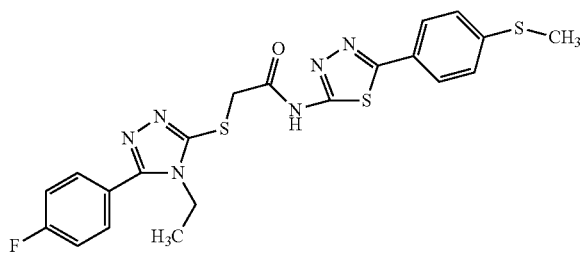 [SMILES: CCn1c(SCC(=O)Nc2nnc(-c3ccc(SC)cc3)s2)nnc1-c1ccc(F)cc1]

2-{[4-ethyl-5-(4-fluorophenyl)-4H-1,2,4-triazol-3-yl]sulfanyl}-N-{5-[4-(methylsulfanyl)phenyl]-1,3,4-thiadiazol-2-yl}acetamid LC-MS (ES): 487.0 (M+H), $^1$H NMR (400 MHz, DMSO-$d_6$) δ 7.87 (d, 2H), 7.70 (dd, 2H), 7.45-7.35 (m, 4H), 4.36 (s, 2H), 4.02 (q, 2H), 2.53 (s, 3H), 1.23 (t, 3H).

Example 56

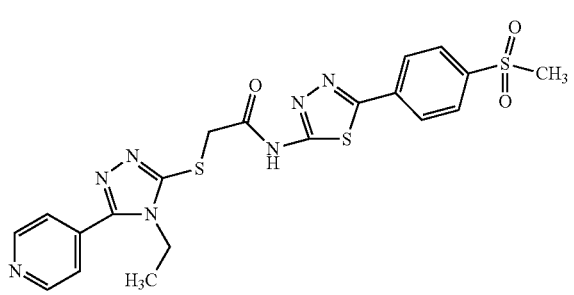 [SMILES: CCn1c(SCC(=O)Nc2nnc(-c3ccc(S(C)(=O)=O)cc3)s2)nnc1-c1ccncc1]

2-{[4-ethyl-5-(pyridin-4-yl)-4H-1,2,4-triazol-3-yl]sulfanyl}-N-[5-(4-methanesulfonylphenyl)-1,3,4-thiadiazol-2-yl]acetamid LC-MS (ES): 502.1 (M+H), $^1$H NMR (400 MHz, DMSO-$d_6$) δ 8.79 (d, 2H), 8.22 (d, 2H), 8.06 (d, 2H), 7.73 (d, 2H), 4.42 (s, 2H), 4.13 (q, 2H), 3.28 (s, 3H), 1.28 (t, 3H).

Example 57

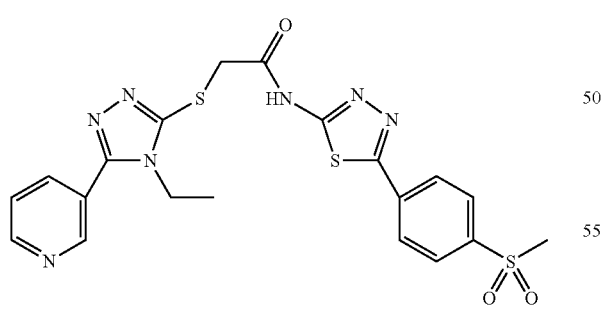

2-{[4-ethyl-5-(pyridin-3-yl)-4H-1,2,4-triazol-3-yl]sulfanyl}-N-[5-(4-methanesulfonylphenyl)-1,3,4-thiadiazol-2-yl]acetamide LC-MS (ES): 502.1 (M+H), $^1$H NMR (400 MHz, DMSO-$d_6$) δ 8.86 (s, 1H), 8.77 (d, 1H), 8.23 (d, 2H), 8.12 (d, 1H), 8.06 (d, 2H), 7.66-7.58 (m, 1H), 4.41 (s, 2H), 4.06 (q, 2H), 3.28 (s, 3H), 1.26 (t, 3H).

ADDITIONAL EXAMPLES

Compounds of Formula (I) wherein $R^7$ is $S(O)(NR^{8a})(R^{8b})$ and wherein $R^{8a}$ is selected from H, $C_1$-$C_6$ alkyl, and $C_3$-$C_6$ cycloalkyl; and $R^{8b}$ is $C_1$-$C_6$ alkyl or $C_3$-$C_6$ cycloalkyl may be prepared as set out in Scheme 1 below.

Scheme 1

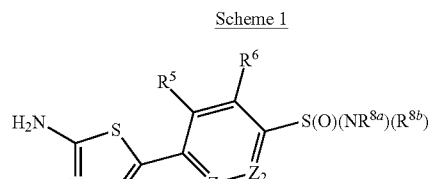

(II)

chloroacetyl chloride, dioxane, TEA, see e.g. synthesis of intermediates 9-14

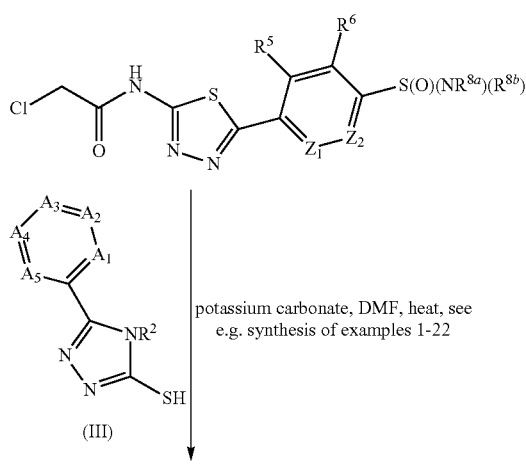

potassium carbonate, DMF, heat, see e.g. synthesis of examples 1-22

Compounds of Formula (I) where $R^7$ is $S(O)(NR^{8a})(R^{8b})$

Examples of intermediates of formula (II) include (IIa-c):

(IIa)

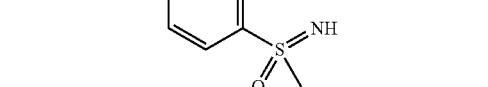

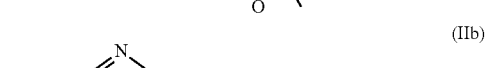

(IIb)

(IIc)

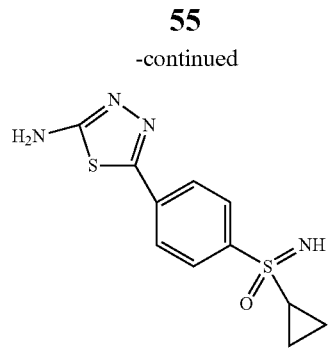

which may be prepared using the procedures as described in "General synthetic strategies towards N-alkyl sulfoximine building blocks for medicinal chemistry and the use of dimethylsulfoximine as a versatile precursor" *Tetrahedron* 2014, 70(37), 6613-6622, and "Synthesis and structure-activity relationship of potent, selective and orally active anthranilamide-based factor Xa inhibitors: Application of weakly basic sulfoximine group as novel S4 binding element" *European Journal of Medicinal Chemistry* 2012, 58, 136-152. A summary is depicted in Scheme 2 immediately below.

Scheme 2

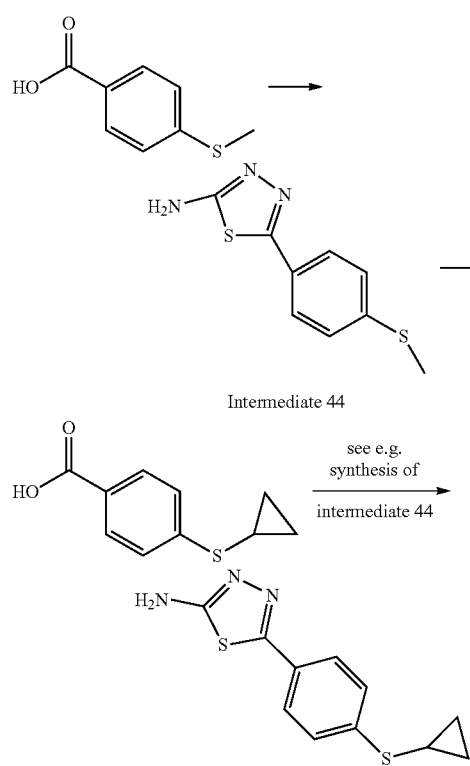

Examples of intermediates of formula (III) include intermediates 6 and 31 described above as well as (IIIa-b):

(IIIa)(IIIb)

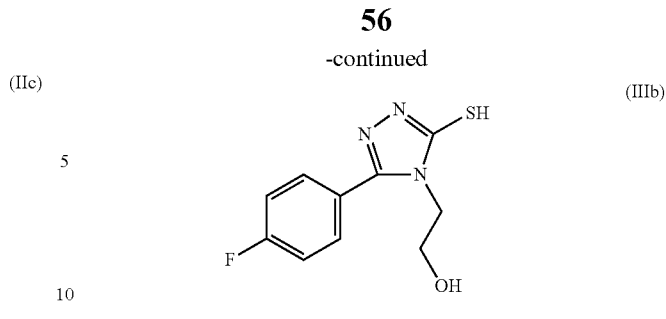

which may be prepared in the same manner as intermediates 6 and 31.

Examples of compounds of Formula (I) wherein $R^7$ is $S(O)(NR^{8a})(R^{8b})$ that can be made using the procedure in Scheme 1 are:

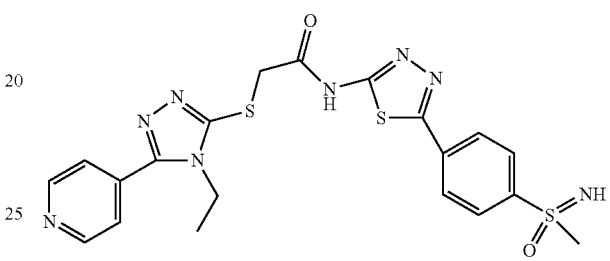

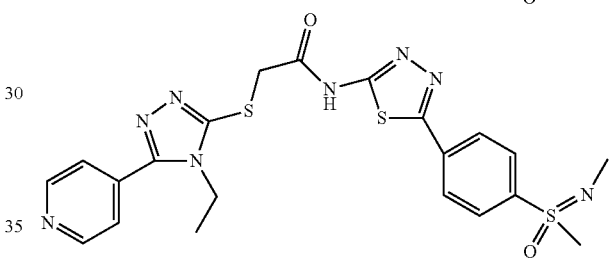

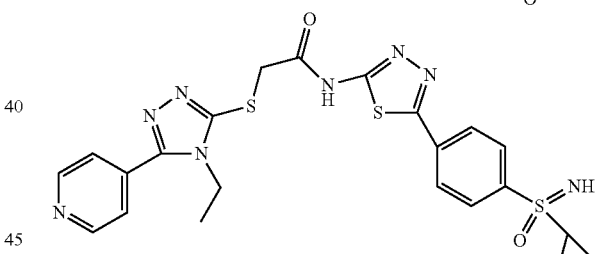

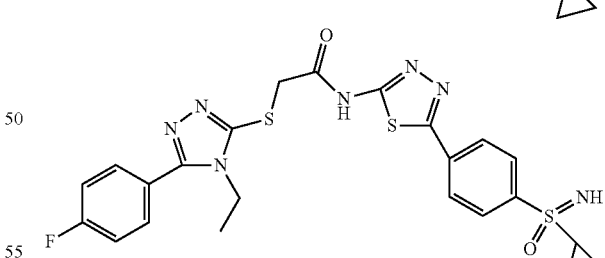

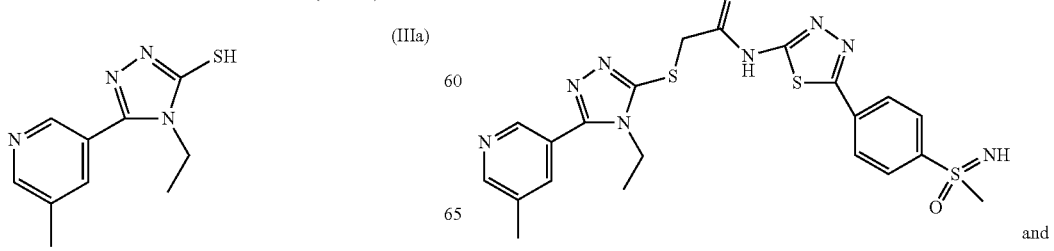

and

-continued

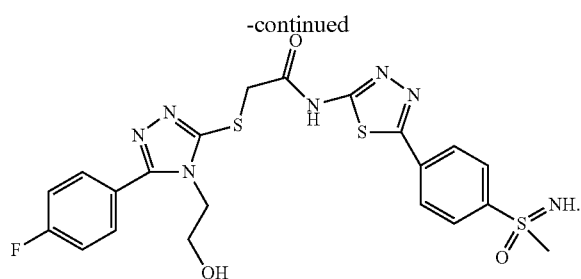

Biological Evaluation
Calcein Quenching Fluostar Assay

A calcein quenching fluostar assay was performed in order to investigate the biological activity of the newly synthesized examples 1 to 57. This type of assay is disclosed in J. Biol. Chem., 2011, 286, 44319-44325 and *Am. J. Physiol. Renal Physiol.* (2010), 298, F224-230.

The buffers used in the assay were prepared with the following compounds and quantities.

500 ml of 4× Buffer:
3.2 mM $MgSO_4.7H_2O$ (0.395 g)
20 mM KCl (0.746 g)
7.2 mM $CaCl\ 2H_2O$ (0.530 g)
100 mM NaHepes (13.02 g)
pH 7.4 w. HCl
Tetracyclin Stock:

|  | Wash buffer (µl) | Sucrose buffer (µl) |
|---|---|---|
| 4× buffer | 80000 | 35000 |
| NaCl (1M) | 34080 | 14910 |
| $H_2O$ | 199520 | 18970 |
| Probenecid | 6400 | 2800 |
| Sucrose (1M) | 0 | 68320 |
| Total | 320000 | 140000 |

The total probenecid required to prepare the wash buffer and sucrose buffer is 6400+2800=9200 µl. An additional 500 µl of probenecid (5 plates at 100 µl each) is also required. Therefore, the total probenecid required is 9200 µl+500 µl=9700 µl. Sufficient probenecid is prepared using:
690 mg probenecid;
4850 µl NaOH 1M;
1213 µl 4× buffer; and
3638 µl $H_2O$.

Assay Experimental Protocol:

1) Two days prior to commencement of the assay, seed 10,000 cells/well of 96 well black clear bottom plate (Greiner Poly-lysin plate). A 1:1 mix of Dulbecco's Modified Eagle's Medium:Nutrient Mixture F-12 (DMEM: F12) was obtained from Gibco. Tetracycline stock of 5 mg/ml in 96% ethanol is used. Medium:DMEM/F12/10% Donor Bovine Serum, Human AQP9 cell line+1:270,000 tetracyclin, mouse AQP9 cell line+1:2,700,000 tetracycline.

2) Day of assay: Flick/slam off the medium and add 50 µl/well of loading solution: 5 ml DMEM/F12/10% Donor Bovine Serum, 25 µl Calcein AM—from freshly dissolved aliquot in 50 µl DMSO (VWR #734-1434), and 100 µl Probenecid.

3) Incubate the well for 90 minutes at 37° C.
4) Perform one wash with 75 µl wash buffer.
5) Add 75 µl of an example compound prepared in wash buffer per well.

Example compounds are prepared in 500 µl U bottom PP plates (NUNC). 2.7 µl Substance in DMSO are added to row A; 180 µl of wash buffer+1% DMSO are added to rows B-H. 90 µl from row A are transferred and mixed with all other wells (up to row G) to make a 3-fold dilution series.

6) Assay in FLUOstar Optima at 25° C. Settings buffer addition at 135 µl seconds, add 75 µl/well, record time course for 30 seconds, add sucrose buffer 3.6 seconds into recording.

7) Normalization to initial in Excel.
8) Fit to "exponential decay" function in GraphPad Prism 5.0, then arrange half live shrinking values according to wells and fit dose-response curves.

The assay results displayed in table 1 below.

TABLE 1

IC50 (nM) values of examples 1 to 57 in the inhibition of human aquaporin 9.

| Example No. | Human AQP9 IC50 (nM) |
|---|---|
| 1 | 393 |
| 2 | 193 |
| 3 | 1289 |
| 4 | 4744 |
| 5 | 4833 |
| 6 | 253 |
| 7 | 260 |
| 8 | 157 |
| 9 | 112 |
| 10 | 37 |
| 11 | 40 |
| 12 | 56 |
| 13 | 323 |
| 14 | 172 |
| 15 | 262 |
| 16 | 269 |
| 17 | 139 |
| 18 | 135 |
| 19 | 233 |
| 20 | 56 |
| 21 | 68 |
| 22 | 160 |
| 23 | 372 |
| 24 | 427 |
| 25 | 375 |
| 26 | 477 |
| 27 | 366 |
| 28 | 200 |
| 29 | 427 |
| 30 | 110 |
| 31 | 99 |
| 32 | 416 |
| 33 | 978 |
| 34 | 61 |
| 35 | 301 |
| 36 | 129 |
| 37 | 82 |
| 38 | 190 |
| 39 | 113 |
| 40 | 810 |
| 41 | 260 |
| 42 | 620 |
| 43 | 92 |
| 44 | 168 |
| 45 | 182 |
| 46 | 385 |
| 47 | 114 |
| 48 | 117 |
| 49 | 373 |
| 50 | 200 |
| 51 | 86 |
| 52 | 59 |
| 53 | 134 |
| 54 | 901 |
| 55 | 676 |
| 56 | 151 |
| 57 | 133 |

In summary, compounds of the present invention have been found to display a very high level of human aquaporin 9 inhibition. The compounds of the present invention are thus deemed to be highly useful in the treatment of diabetes.

The invention claimed is:

1. A compound of Formula (I)

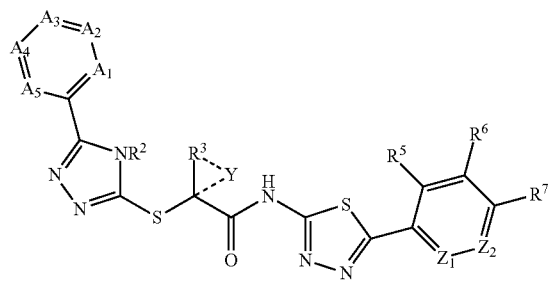

Formula (I)

or a pharmaceutically acceptable salt or stereoisomers thereof, wherein:

$A_1, A_2, A_3, A_4,$ and $A_5$ are independently selected from the group consisting of CH, $CR^1$ and N;

Y is absent or is selected from $CH_2$ or $CHC_1$-$C_5$ alkyl;

- - - -. is a single bond when Y is $CH_2$ or $CHC_1$-$C_5$ alkyl;

$Z_1$ and $Z_2$ are independently selected from the group consisting of CH and N;

$R^1$ is independently selected from the group consisting of halogen, CN, OH, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^2$ is selected from the group consisting of $C_1$-$C_6$ alkyl, $C_1$-$C_6$ alkylene-$OR^{4a}$, $C_1$-$C_6$ alkylene-$N(R^{4a})(R^{4b})$, $C_1$-$C_6$ alkylene-$C(O)N(R^{4a})(R^{4b})$, $C_1$-$C_6$ alkylene-C(O)$OR^{4a}$, $C_1$-$C_3$ alkylene-$C_3$-$C_6$ cycloalkyl, and $C_3$-$C_5$ cycloalkyl;

$R^3$ is selected from the group consisting of H, $C_1$-$C_6$ alkyl, and $C_1$-$C_6$ alkylene-C(O)$N(R^{4a})(R^{4b})$ when Y is absent or, $R^3$ is selected from $C_1$-$C_6$ alkyl, and $C_1$-$C_6$ alkylene-C(O)$N(R^{4a})(R^{4b})$ when Y is $CH_2$ or $CHC_1$-$C_5$ alkyl;

$R^{4a}$ and $R^{4b}$ are independently selected from H, $C_1$-$C_4$ alkyl, and cyclopropyl;

$R^5$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^6$ is selected from the group consisting of H, F, $C_1$-$C_6$ alkyl, $C_1$-$C_3$ alkylene-$C_3$-$C_6$ cycloalkyl, $C_3$-$C_6$ cycloalkyl, and $C_1$-$C_6$ alkyloxy;

$R^7$ is selected from the group consisting of H, halogen, CN, OH, $C_1$-$C_6$ alkyl, $C_3$-$C_6$ cycloalkyl, $C_1$-$C_6$ alkyloxy, $O(CH_2)_mO(CH_2)_nCH_3$, $O(CH_2)_mN(R^{4a})(R^{4b})$, $OSO_2CH_3$, $SO_2C_1$-$C_6$ alkyl, $C_1$-$C_6$ alkylene-$SO_2C_1$-$C_6$ alkyl, $SO_2C_3$-$C_6$ cycloalkyl, $C_1$-$C_6$ alkylene-$SOC_3$-$C_6$ cycloalkyl, $SC_1$-$C_6$ alkyl, $SC_3$-$C_6$ cycloalkyl, $C_1$-$C_6$ alkylene-$SC_1$-$C_6$ alkyl, $C_1$-$C_6$ alkylene-$SC_3$-$C_6$ cycloalkyl, and $S(O)(NR^{8a})(R^{8b})$;

$R^{8a}$ is selected from H, $C_1$-$C_6$ alkyl, and $C_3$-$C_6$ cycloalkyl;

$R^{8b}$ is $C_1$-$C_6$ alkyl or $C_3$-$C_6$ cycloalkyl;

m is an integer selected from the group consisting of 1, 2, and 3; and n is an integer selected from the group consisting of 0, 1, and 2;

with the proviso that $R^5$, $R^6$, and $R^7$ cannot be H simultaneously; and with the proviso that the compound is not any of:

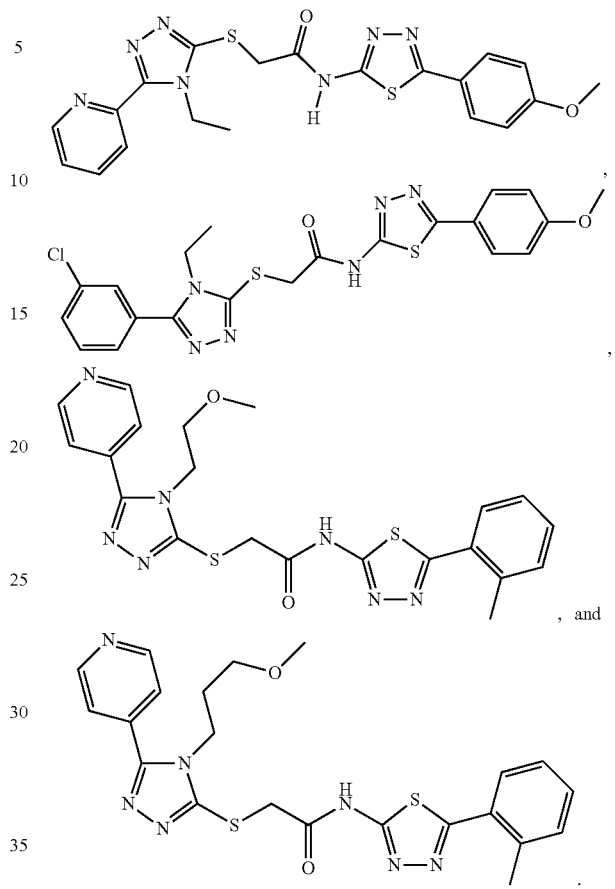

2. The compound of claim 1, wherein $R^1$ is independently selected from the group consisting of F, Cl, $CH_3$, and $OCH_3$.

3. The compound of claim 1, wherein $R^2$ is selected from the group consisting of $CH_3$, $CH_2CH_3$, and cyclopropyl.

4. The compound of claim 1, wherein $R^2$ is selected from the group consisting of $CH_2CH_2OH$, $CH_2CH_2CH_2OH$, $CH_2CH_2NH_2$, $CH_2C(O)NH_2$, and $CH_2CH_2C(O)OCH_3$.

5. The compound of claim 1, wherein $R^3$ is H.

6. The compound of claim 1, wherein $R^{4a}$ and $R^{4b}$ are independently selected from H and $CH_3$.

7. The compound of claim 1, wherein at least one of $R^5$ and $R^6$ is independently selected from the group consisting of H, F, and $OCH_3$.

8. The compound of claim 1, wherein $R^7$ is selected from the group consisting of H, halogen, CN, OH, $C_1$-$C_6$ alkyl, $C_3$-$C_6$ cycloalkyl, $C_1$-$C_6$ alkyloxy, $O(CH_2)_mO(CH_2)_nCH_3$, $O(CH_2)_mN(R^{4a})(R^{4b})$, and $OSO_2CH_3$.

9. The compound of claim 1, wherein $R^7$ is selected from the group consisting of H, F, OH, $OCH_3$, $OCH_2CH_2OCH_3$, and $OSO_2CH_3$.

10. The compound of claim 1, wherein $R^7$ is selected from the group consisting of $SO_2CH_3$, $CH_2SO_2CH_3$, $SCH_3$, $S(O)(NH)CH_3$, $S(O)(NCH_3)CH_3$, $S(O)(NH)$cyclopropyl, and $S(O)(NCH_3)$cyclopropyl.

11. The compound of claim 1, wherein Y is absent.

12. The compound of claim 1, wherein the compound is selected from the group consisting of:

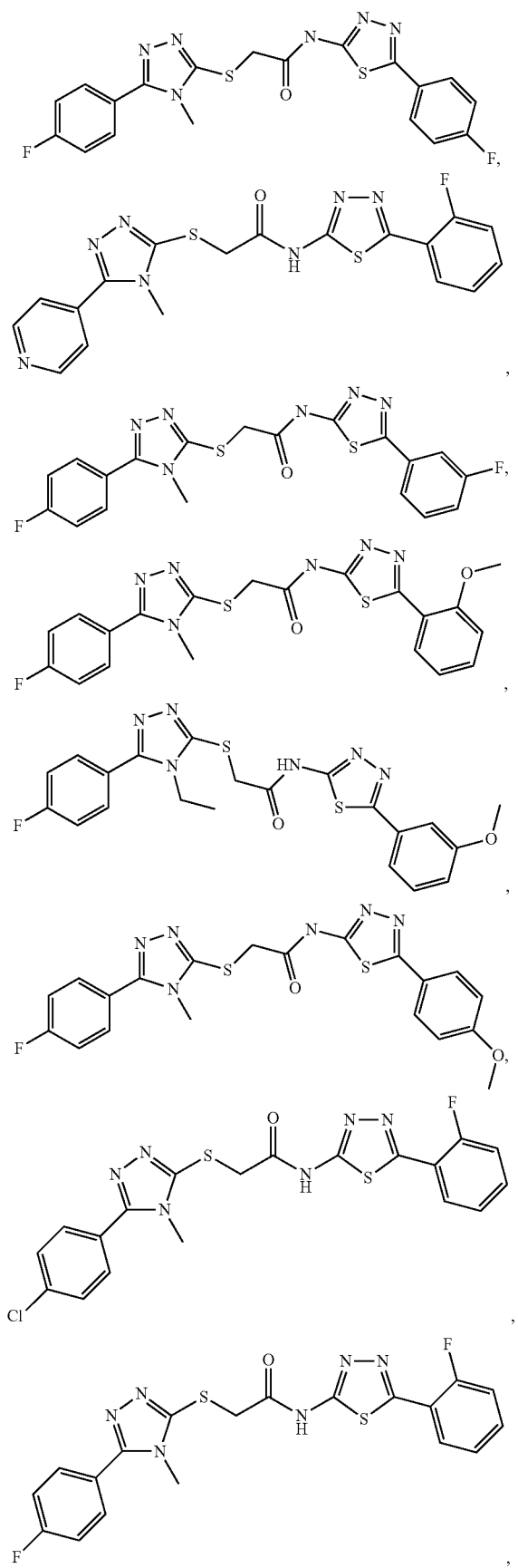

-continued
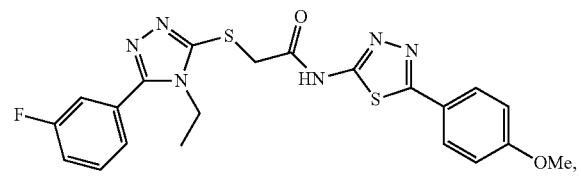
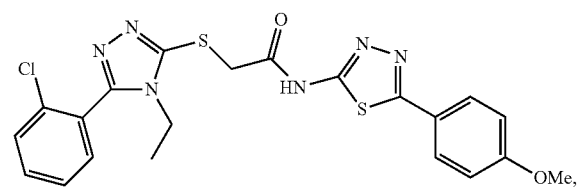
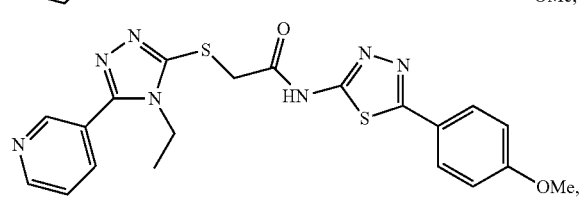
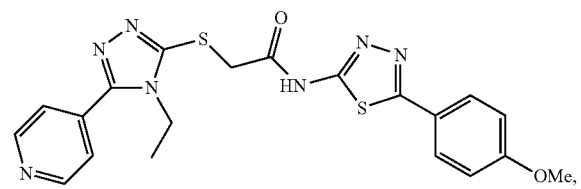
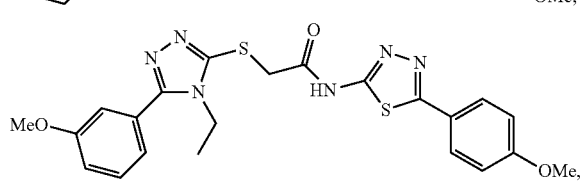
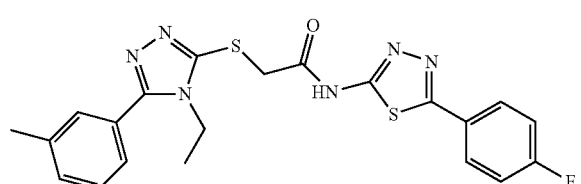
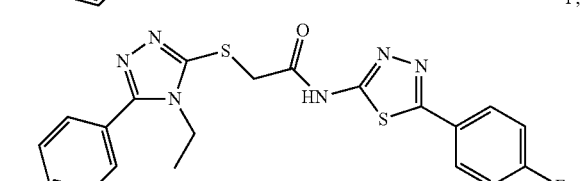
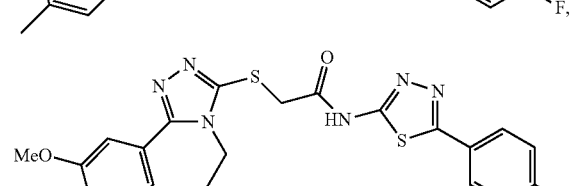
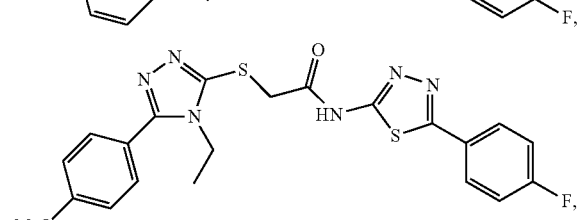
-continued
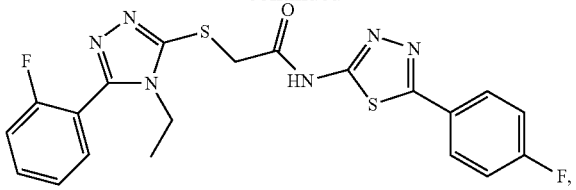
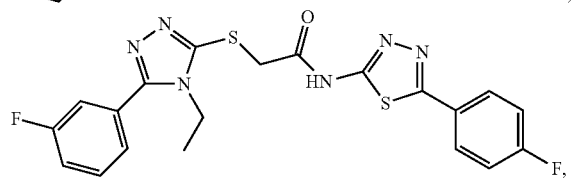
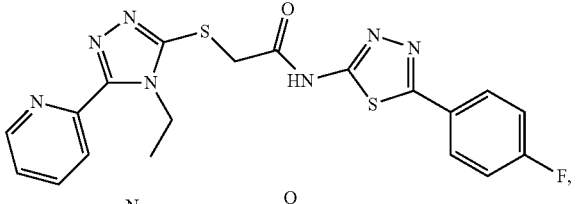
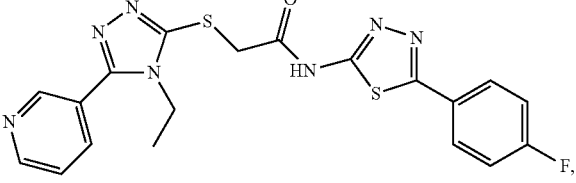
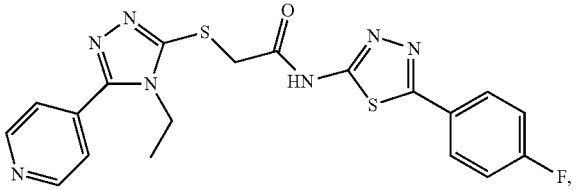
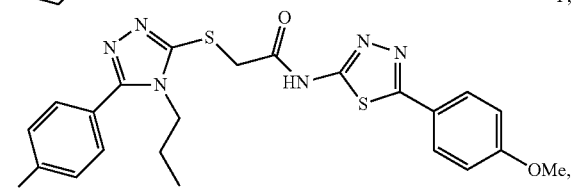
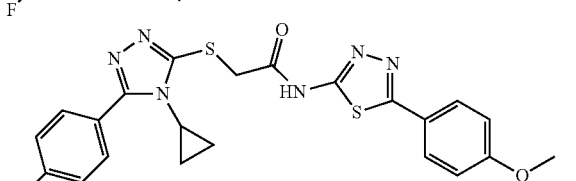
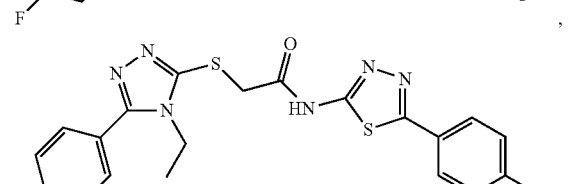
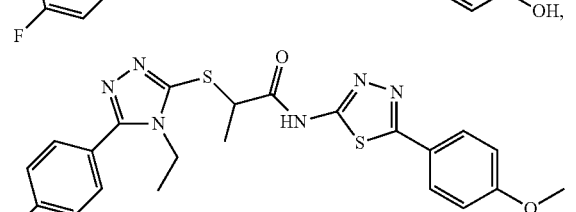

-continued
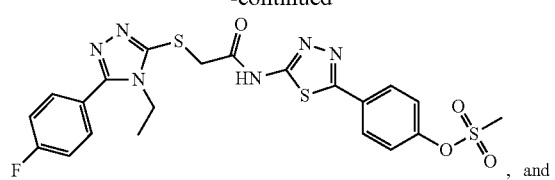, and
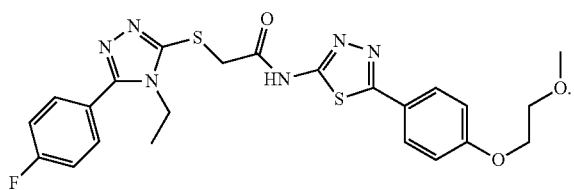
13. The compound of claim 1, wherein the compound is selected from the group consisting of:
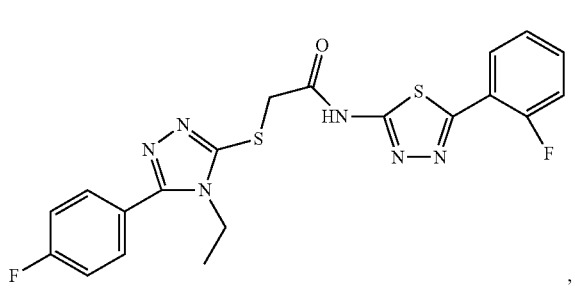,
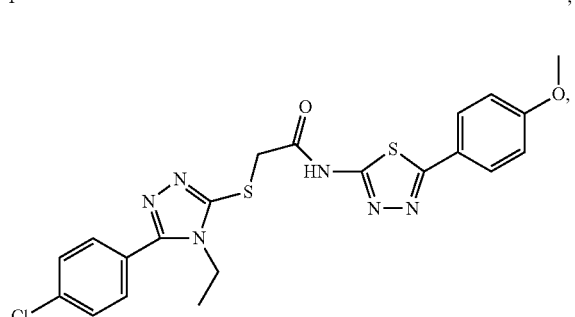,
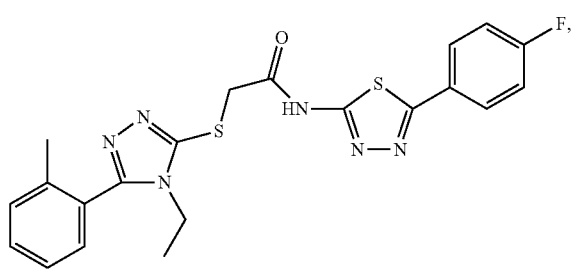,
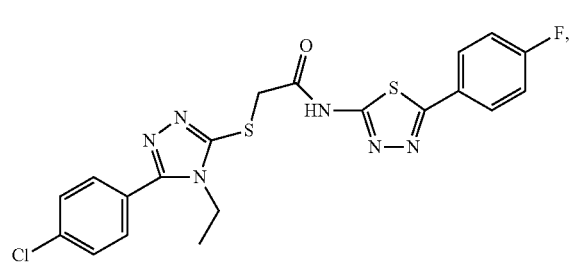,
-continued
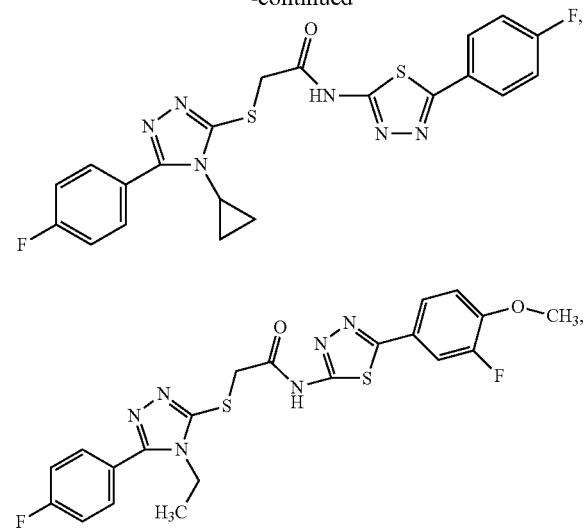
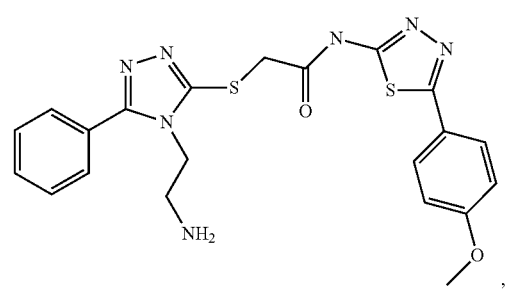,

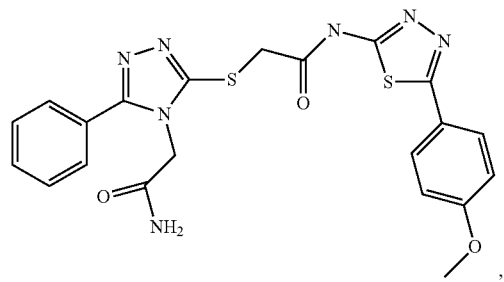
, 
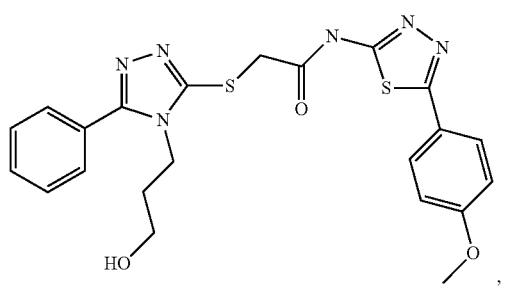
, and
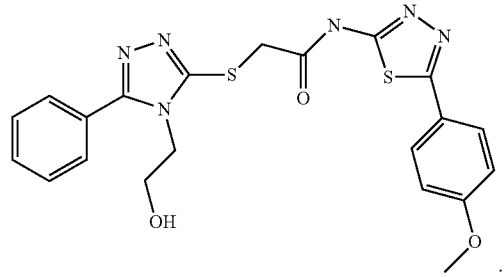
.
14. The compound of claim 1, wherein the compound is selected from the group consisting of:
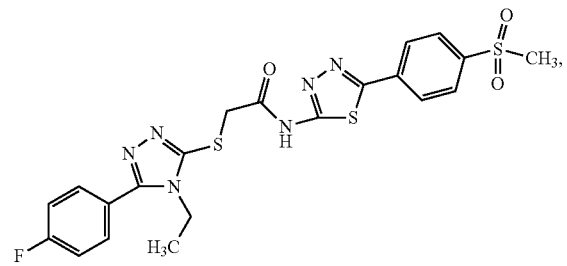
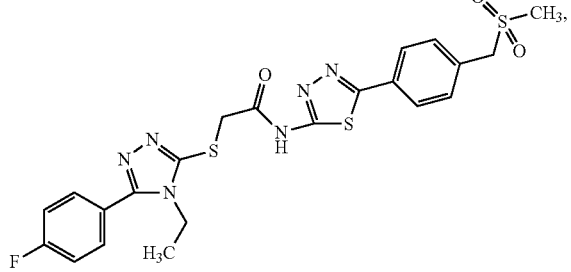
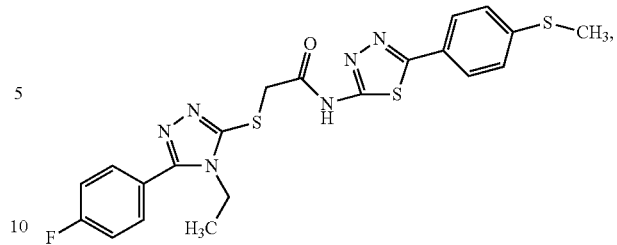
,
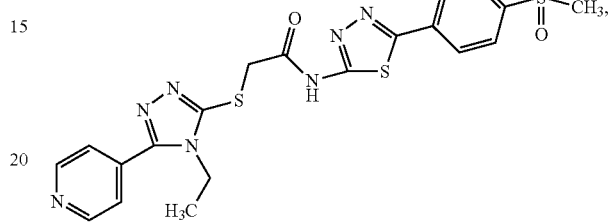
,
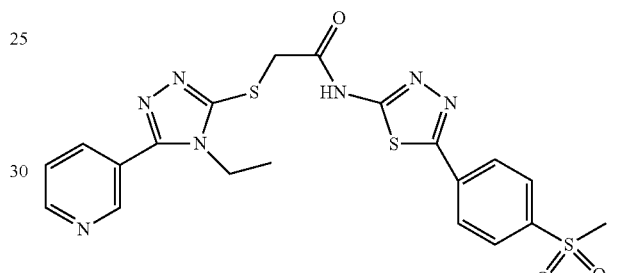
,
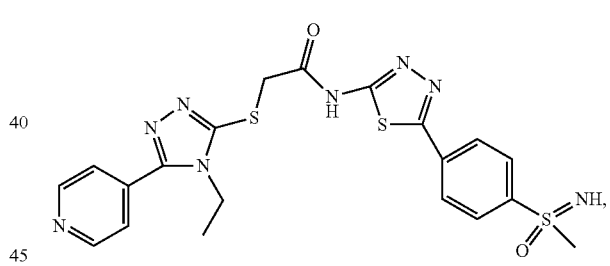
,
,
, -continued

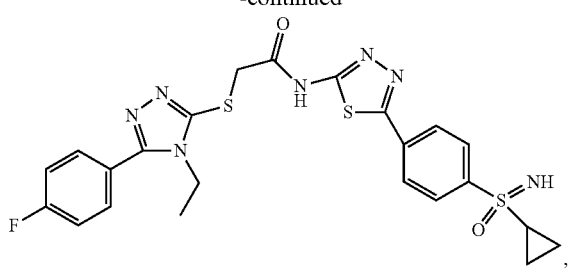

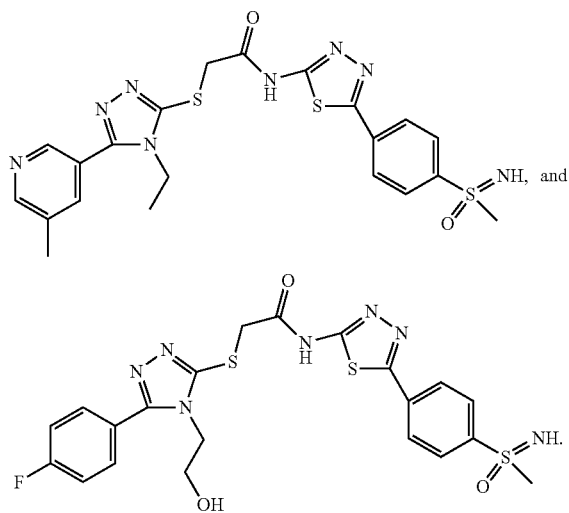

15. A pharmaceutical composition comprising the compound of claim 1 and a pharmaceutically acceptable diluent, excipient or carrier.

16. A method of treating diabetes, comprising administering to a subject in need thereof a composition comprising the compound of claim 1.

17. The method of claim 16, wherein the diabetes is type-2 diabetes.

18. A method of treating a disorder or disease, wherein the function or dysfunction of AQP9 contributes to the development or maintenance of the disorder or disease, comprising administering to a subject in need thereof a composition comprising the compound of claim 1.

19. The method of claim 18, wherein the disorder or disease is selected from the group consisting of diabetes, atherosclerosis, disuse osteoporosis, non-alcoholic fatty liver disease, an inflammatory diseases, inflammatory bowel disease, psoriasis, rheumatoid arthritis, a kidney injury, a kidney ischemia-reperfusion injury, and allergic contact dermatitis.

* * * * *